US009895505B2

(12) United States Patent
Guney

(10) Patent No.: US 9,895,505 B2
(45) Date of Patent: Feb. 20, 2018

(54) NASAL ASSEMBLY

(71) Applicant: ResMed Limited, Bella Vista, New South Wales (AU)

(72) Inventor: Memduh Guney, Sydney (AU)

(73) Assignee: ResMed Limited, Bella Vista (AU)

( * ) Notice: Subject to any disclaimer, the term of this patent is extended or adjusted under 35 U.S.C. 154(b) by 929 days.

(21) Appl. No.: 14/259,406

(22) Filed: Apr. 23, 2014

(65) Prior Publication Data

US 2014/0261433 A1 Sep. 18, 2014

Related U.S. Application Data

(63) Continuation of application No. 12/926,213, filed on Nov. 2, 2010, now Pat. No. 8,757,162, which is a continuation of application No. 11/101,657, filed on Apr. 8, 2005, now Pat. No. 7,942,150.

(60) Provisional application No. 60/560,610, filed on Apr. 9, 2004, provisional application No. 60/632,193, filed on Dec. 2, 2004.

(51) Int. Cl.
*A61M 16/06* (2006.01)
*A61M 16/00* (2006.01)
*A61M 16/08* (2006.01)

(52) U.S. Cl.
CPC ........ *A61M 16/0066* (2013.01); *A61M 16/06* (2013.01); *A61M 16/0666* (2013.01); *A61M 16/0683* (2013.01); *A61M 16/0825* (2014.02); *A61M 16/0611* (2014.02); *A61M 2210/0618* (2013.01)

(58) Field of Classification Search
CPC .......... A61M 16/0066; A61M 16/0666; A61M 16/06; A61M 16/0611; A61M 16/0683; A61M 16/0825; A61M 2202/0085; A61M 2202/0225; A61M 2205/42; A61M 2210/18; A62B 18/02; A62B 18/10

See application file for complete search history.

(56) References Cited

U.S. PATENT DOCUMENTS

| 11,914 A | 11/1854 | Browne | |
|---|---|---|---|
| 123,776 A * | 2/1872 | Goodale | F16L 37/025 |
| | | | 285/66 |
| 443,191 A | 12/1890 | Illing | |
| 781,516 A | 1/1905 | Guthrie | |

(Continued)

FOREIGN PATENT DOCUMENTS

| AU | 91/77110 B | 11/1991 |
|---|---|---|
| AU | 94/64816 B | 12/1994 |

(Continued)

OTHER PUBLICATIONS

J.P. Tullis, "Cavitation Guide for Control Valves", Published Apr. 1993; retrieved from https://www.osti.gov/scitech/servlets/purl/10155405.*

(Continued)

*Primary Examiner* — Tan-Uyen (Jackie) T Ho
*Assistant Examiner* — Joseph D Boecker
(74) *Attorney, Agent, or Firm* — Nixon & Vanderhye P.C.

(57) ABSTRACT

A vent assembly includes at least one vent having a first end configured to face atmosphere and a second end opposite the first end, and a central portion provided between the first and second ends including a substantially cylindrical cross-sectional shape, wherein the second end includes a counter bore.

10 Claims, 45 Drawing Sheets

(56) References Cited

U.S. PATENT DOCUMENTS

| | | |
|---|---|---|
| 812,706 A | 2/1906 | Warbasse |
| 835,075 A | 11/1906 | Mahaffy |
| 1,443,820 A | 1/1923 | Hudson |
| 1,599,111 A | 9/1926 | Beadle |
| 1,653,572 A | 12/1927 | Jackson |
| 1,706,602 A | 3/1929 | Alexander et al. |
| 1,926,027 A | 9/1933 | Biggs |
| 2,008,677 A | 7/1935 | Booharin |
| 2,102,037 A | 12/1937 | Schwartz |
| 2,123,353 A | 7/1938 | Catt |
| 2,248,477 A | 7/1941 | Lombard |
| 2,254,854 A | 9/1941 | O'Connell |
| 2,259,817 A | 10/1941 | Hawkins |
| 2,317,608 A | 4/1943 | Heidbrink |
| 2,371,965 A | 3/1945 | Lehmberg |
| 2,376,871 A | 5/1945 | Fink |
| 2,415,846 A | 2/1947 | Randall |
| 2,438,058 A | 3/1948 | Kincheloe |
| 2,578,621 A | 12/1951 | Yant |
| 2,843,121 A | 7/1958 | Hudson |
| 2,858,828 A | 11/1958 | Matheson |
| 2,872,923 A | 2/1959 | Birch et al. |
| 2,931,356 A | 4/1960 | Schwarz |
| D188,084 S | 5/1960 | Garelick |
| 2,939,468 A | 6/1960 | Lundquist |
| 3,013,556 A | 12/1961 | Gaiieher |
| 3,162,411 A | 12/1964 | Duggan |
| 3,182,659 A | 5/1965 | Blount |
| 3,189,027 A | 6/1965 | Bartlett |
| 3,238,943 A | 3/1966 | Holley |
| 3,291,127 A | 12/1966 | Eimer et al. |
| 3,315,674 A | 4/1967 | Bloom et al. |
| 3,330,273 A | 7/1967 | Bennett |
| 3,343,563 A * | 9/1967 | Carter, Jr. ............... A62B 9/022 |
| | | 137/505.18 |
| 3,362,420 A | 1/1968 | Blackburn et al. |
| 3,363,833 A | 1/1968 | Laerdal |
| 3,412,231 A | 11/1968 | McElligott |
| 3,490,452 A | 1/1970 | Greenfield |
| 3,513,844 A | 5/1970 | Smith |
| 3,518,332 A | 6/1970 | Sklarchuk et al. |
| 3,542,020 A * | 11/1970 | Bushman ............... A61M 16/00 |
| | | 128/204.24 |
| 3,556,122 A | 1/1971 | Laerdal |
| 3,580,051 A | 5/1971 | Blevins |
| 3,680,556 A | 8/1972 | Morgan |
| 3,700,000 A | 10/1972 | Hesse et al. |
| 3,720,235 A | 3/1973 | Schrock |
| 3,754,552 A | 8/1973 | King |
| 3,762,747 A | 10/1973 | Griffen |
| 3,796,216 A | 3/1974 | Schwarz |
| 3,799,164 A | 3/1974 | Rollins |
| 3,807,432 A * | 4/1974 | Cain ............... F16K 15/207 |
| | | 137/224 |
| D231,803 S | 6/1974 | Huddy |
| 3,850,171 A | 11/1974 | Ball et al. |
| 3,868,164 A | 2/1975 | Lisk |
| 3,877,425 A | 4/1975 | O'Neill |
| 3,942,403 A | 3/1976 | Pramberger |
| 3,949,743 A | 4/1976 | Shanbrom |
| 3,958,275 A | 5/1976 | Morgan et al. |
| 3,964,570 A * | 6/1976 | Morrow ............... F01N 1/10 |
| | | 181/268 |
| 4,037,142 A | 7/1977 | Poole |
| 4,077,404 A | 3/1978 | Elam |
| D250,131 S | 10/1978 | Lewis et al. |
| 4,137,602 A | 2/1979 | Klumpp, Jr. |
| 4,167,185 A | 9/1979 | Lewis |
| 4,201,205 A | 5/1980 | Bartholomew |
| 4,219,020 A | 8/1980 | Czajka |
| 4,226,234 A | 10/1980 | Gunderson |
| 4,245,632 A | 1/1981 | Houston |
| 4,248,218 A | 2/1981 | Fischer |
| 4,258,710 A | 3/1981 | Reber |
| 4,266,540 A | 5/1981 | Panzik et al. |
| 4,274,406 A | 6/1981 | Bartholomew |
| 4,276,877 A | 6/1981 | Gdulla |
| D262,322 S | 12/1981 | Mizerak |
| 4,304,229 A | 12/1981 | Curtin |
| 4,326,797 A | 5/1982 | Rollins, III et al. |
| 4,328,797 A | 5/1982 | Rollins, III et al. |
| 4,347,205 A | 8/1982 | Stewart |
| 4,354,488 A | 10/1982 | Bartos |
| 4,363,238 A * | 12/1982 | Willam ............... A61B 5/0878 |
| | | 600/537 |
| 4,363,580 A | 12/1982 | Bell |
| 4,402,316 A | 9/1983 | Gadberry |
| 4,412,537 A | 11/1983 | Tiger |
| 4,428,392 A * | 1/1984 | Jones ............... A61M 16/208 |
| | | 128/205.24 |
| 4,440,163 A | 4/1984 | Spergel |
| 4,454,881 A | 6/1984 | Huber et al. |
| 4,467,799 A | 8/1984 | Steinberg |
| 4,522,639 A | 6/1985 | Ansite et al. |
| 4,535,767 A | 8/1985 | Tiep et al. |
| 4,558,708 A * | 12/1985 | Labuda ............... A61M 16/08 |
| | | 128/207.14 |
| 4,558,710 A | 12/1985 | Eichler |
| 4,559,939 A | 12/1985 | Levine et al. |
| 4,580,556 A | 4/1986 | Kondur |
| 4,603,692 A | 8/1986 | Montesi |
| 4,616,647 A | 10/1986 | McCreadie |
| 4,622,964 A | 11/1986 | Flynn |
| 4,648,394 A | 3/1987 | Wise |
| 4,655,213 A | 4/1987 | Rapoport et al. |
| 4,649,912 A | 5/1987 | Collins |
| 4,665,570 A | 5/1987 | Davis |
| 4,671,271 A | 6/1987 | Bishop et al. |
| 4,677,975 A | 7/1987 | Edgar et al. |
| 4,677,977 A | 7/1987 | Wilcox |
| D293,613 S | 1/1988 | Wingler |
| 4,730,500 A * | 3/1988 | Hughes ............... A61M 15/00 |
| | | 73/861.22 |
| 4,739,755 A | 4/1988 | White et al. |
| 4,770,169 A | 9/1988 | Schmoegner et al. |
| 4,774,941 A | 10/1988 | Cook |
| 4,774,946 A | 10/1988 | Ackerman |
| 4,782,832 A | 11/1988 | Trimble et al. |
| 4,799,477 A | 1/1989 | Lewis |
| 4,809,692 A | 3/1989 | Nowacki et al. |
| 4,819,629 A | 4/1989 | Jonson |
| 4,821,713 A | 4/1989 | Bauman |
| 4,841,953 A | 6/1989 | Dodrill |
| 4,846,334 A | 7/1989 | Belim |
| 4,848,366 A | 7/1989 | Aita et al. |
| 4,907,584 A | 3/1990 | McGinnis |
| 4,910,806 A | 3/1990 | Baker et al. |
| 4,915,105 A | 4/1990 | Lee |
| 4,919,128 A | 4/1990 | Kopala et al. |
| 4,938,210 A | 7/1990 | Shene |
| 4,938,212 A | 7/1990 | Gnook et al. |
| 4,944,310 A | 7/1990 | Sullivan |
| D310,431 S | 9/1990 | Bellm |
| 4,969,901 A | 11/1990 | Binder |
| 4,971,051 A | 11/1990 | Toffolon |
| 4,974,586 A | 12/1990 | Wandel et al. |
| 4,986,269 A | 1/1991 | Hakkinen |
| 4,989,596 A | 2/1991 | MacRis et al. |
| 4,989,599 A | 2/1991 | Carter |
| 5,005,568 A | 4/1991 | Loescher et al. |
| 5,005,571 A | 4/1991 | Dietz |
| 5,018,519 A | 5/1991 | Brown |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,046,512 A | 9/1991 | Murchie |
| 5,063,922 A | 11/1991 | Hakkinen |
| 5,065,756 A | 11/1991 | Rapoport |
| D322,318 S | 12/1991 | Sullivan |
| 5,069,205 A | 12/1991 | Urso |
| 5,069,222 A | 12/1991 | McDonald, Jr. |
| 5,069,586 A | 12/1991 | Casey |
| 5,080,094 A | 1/1992 | Tayebi |

(56) References Cited

U.S. PATENT DOCUMENTS

| | | | |
|---|---|---|---|
| 5,081,866 A * | 1/1992 | Ochiai | A61B 5/0878 |
| | | | 600/537 |
| D323,908 S | 2/1992 | Hollister et al. | |
| 5,109,839 A | 5/1992 | Blasdell et al. | |
| 5,109,840 A | 5/1992 | Daleiden | |
| 5,117,819 A | 6/1992 | Servidio et al. | |
| 5,121,745 A | 6/1992 | Israel | |
| 5,133,347 A | 7/1992 | Huennebeck | |
| 5,140,982 A | 8/1992 | Bauman | |
| 5,148,802 A | 9/1992 | Sanders et al. | |
| 5,159,938 A | 11/1992 | Laughlin | |
| 5,178,138 A | 1/1993 | Walstrom et al. | |
| D334,633 S | 4/1993 | Rudolph | |
| 5,231,983 A | 8/1993 | Matson et al. | |
| 5,233,978 A | 8/1993 | Callaway | |
| 5,243,971 A | 9/1993 | Sullivan | |
| 5,265,595 A | 11/1993 | Rudolph | |
| 5,269,296 A | 12/1993 | Landis | |
| 5,279,289 A | 1/1994 | Kirk | |
| 5,280,784 A | 1/1994 | Kohler | |
| 5,297,544 A | 3/1994 | May | |
| 5,311,862 A | 5/1994 | Blasdell et al. | |
| 5,322,057 A | 6/1994 | Raabe et al. | |
| 5,343,878 A | 9/1994 | Scarberry et al. | |
| 5,357,951 A | 10/1994 | Ratner | |
| 5,358,340 A | 10/1994 | Bober | |
| 5,368,020 A | 11/1994 | Beux | |
| 5,372,130 A | 12/1994 | Stern et al. | |
| 5,388,571 A | 2/1995 | Roberts et al. | |
| 5,404,871 A | 4/1995 | Goodman et al. | |
| 5,419,318 A | 5/1995 | Tayebi | |
| 5,441,046 A | 6/1995 | Starr et al. | |
| 5,429,126 A | 7/1995 | Bracken | |
| 5,429,683 A | 7/1995 | Le Mitouard | |
| 5,431,158 A | 7/1995 | Tirotta | |
| 5,439,981 A | 8/1995 | Starr et al. | |
| D362,061 S | 9/1995 | McGinnis et al. | |
| 5,477,852 A | 12/1995 | Landis | |
| 5,479,920 A | 1/1996 | Piper et al. | |
| 5,488,948 A | 2/1996 | Dubruille et al. | |
| 5,492,116 A | 2/1996 | Scarberry et al. | |
| 5,501,214 A | 3/1996 | Sabo | |
| 5,509,404 A | 4/1996 | Lloyd et al. | |
| 5,517,986 A | 5/1996 | Starr et al. | |
| 5,533,506 A | 7/1996 | Wood | |
| 5,538,000 A | 7/1996 | Rudolph | |
| 5,540,223 A | 7/1996 | Starr et al. | |
| 5,542,128 A | 8/1996 | Lomas | |
| 5,557,752 A | 9/1996 | Landis et al. | |
| RE35,339 E | 10/1996 | Rapoport | |
| 5,560,354 A | 10/1996 | Berthon-Jones et al. | |
| 5,570,682 A | 11/1996 | Johnson | |
| 5,570,689 A | 11/1996 | Starr et al. | |
| 5,575,277 A | 11/1996 | Lutz et al. | |
| D377,089 S | 12/1996 | Starr et al. | |
| 5,592,938 A | 1/1997 | Scarberry et al. | |
| 5,598,839 A * | 2/1997 | Niles | A61M 16/08 |
| | | | 128/205.23 |
| 5,608,647 A | 3/1997 | Rubsamen et al. | |
| 5,642,730 A | 7/1997 | Baran | |
| 5,645,049 A | 7/1997 | Foley et al. | |
| 5,647,355 A | 7/1997 | Starr et al. | |
| 5,647,357 A | 7/1997 | Barnett et al. | |
| 5,649,532 A | 7/1997 | Oren | |
| 5,649,533 A | 7/1997 | Griffiths | |
| 5,655,520 A | 8/1997 | Howe et al. | |
| 5,655,527 A | 8/1997 | Scarberry et al. | |
| 5,657,493 A | 8/1997 | Ferrero et al. | |
| 5,657,752 A | 8/1997 | Landis et al. | |
| 5,662,101 A | 9/1997 | Ogden et al. | |
| 5,666,946 A | 9/1997 | Langenback | |
| 5,676,132 A * | 10/1997 | Tillotson | A61B 5/0878 |
| | | | 128/204.23 |
| 5,685,296 A | 11/1997 | Zdrojkowski et al. | |
| 5,687,715 A | 11/1997 | Landis et al. | |
| 5,709,204 A | 1/1998 | Lester | |
| 5,715,741 A | 2/1998 | Gasser et al. | |
| 5,715,814 A | 2/1998 | Ebers | |
| 5,724,965 A | 3/1998 | Handke et al. | |
| 5,732,695 A | 3/1998 | Metzger | |
| 5,740,799 A | 4/1998 | Nielsen | |
| 5,746,201 A | 5/1998 | Kidd | |
| 5,765,553 A | 6/1998 | Richards et al. | |
| 5,778,872 A * | 7/1998 | Fukunaga | A61M 16/1055 |
| | | | 128/202.27 |
| 5,813,423 A | 9/1998 | Kirchgeorg | |
| 5,832,918 A | 11/1998 | Pantino | |
| 5,839,433 A | 11/1998 | Higenbottam | |
| 5,843,044 A * | 12/1998 | Moorehead | A61M 16/20 |
| | | | 137/845 |
| 5,857,460 A | 1/1999 | Popitz | |
| 5,878,742 A | 3/1999 | Figueredo et al. | |
| 5,904,334 A * | 5/1999 | Grunert | F16K 31/404 |
| | | | 137/846 |
| 5,918,598 A | 7/1999 | Belfer et al. | |
| 5,921,239 A | 7/1999 | McCall et al. | |
| 5,937,851 A | 8/1999 | Serowski et al. | |
| 6,006,748 A | 12/1999 | Hollis | |
| 6,012,455 A | 1/2000 | Goldstein | |
| 6,019,101 A | 2/2000 | Cotner et al. | |
| 6,039,044 A | 3/2000 | Sullivan | |
| 6,044,844 A | 4/2000 | Kwok et al. | |
| 6,112,746 A | 9/2000 | Kwok et al. | |
| 6,119,693 A | 9/2000 | Kwok et al. | |
| 6,119,694 A | 9/2000 | Correa et al. | |
| 6,135,109 A | 10/2000 | Blasdell et al. | |
| 6,192,886 B1 | 2/2001 | Rudolph | |
| 6,216,692 B1 * | 4/2001 | Todokoro | A61B 5/097 |
| | | | 128/204.23 |
| 6,309,438 B1 | 10/2001 | Kanno et al. | |
| 6,431,172 B1 | 8/2002 | Bordewick | |
| 6,435,181 B1 * | 8/2002 | Jones, Jr. | A61M 16/06 |
| | | | 128/204.18 |
| 6,478,026 B1 | 11/2002 | Wood | |
| 6,561,190 B1 | 5/2003 | Kwok | |
| 6,561,191 B1 | 5/2003 | Kwok | |
| 6,581,594 B1 | 6/2003 | Drew et al. | |
| 6,581,595 B1 * | 6/2003 | Murdock | A61B 5/083 |
| | | | 128/204.18 |
| 6,584,976 B2 | 7/2003 | Japuntich et al. | |
| 6,595,215 B2 | 7/2003 | Wood | |
| 6,644,308 B2 | 11/2003 | Kalhok et al. | |
| 6,644,316 B2 * | 11/2003 | Bowman | A61M 16/06 |
| | | | 128/205.24 |
| 6,655,385 B1 | 12/2003 | Curti et al. | |
| 6,662,803 B2 * | 12/2003 | Gradon | A61M 16/1095 |
| | | | 128/205.25 |
| 6,668,830 B1 * | 12/2003 | Hansen | A62B 18/10 |
| | | | 128/206.21 |
| 6,679,265 B2 | 1/2004 | Strickland et al. | |
| 6,792,623 B2 | 9/2004 | Luppi | |
| 6,807,967 B2 | 10/2004 | Wood | |
| 6,823,865 B2 | 11/2004 | Drew et al. | |
| 6,935,460 B2 * | 8/2005 | McCombs | B01D 39/083 |
| | | | 181/222 |
| 7,159,587 B2 | 1/2007 | Drew et al. | |
| 7,178,538 B2 | 2/2007 | Lau et al. | |
| 7,207,335 B2 | 4/2007 | Kwok et al. | |
| 7,210,477 B2 | 5/2007 | Templeton et al. | |
| 7,370,652 B2 | 5/2008 | Matula et al. | |
| 7,650,884 B2 | 1/2010 | Flannigan et al. | |
| 7,942,150 B2 | 5/2011 | Guney et al. | |
| 8,439,035 B2 * | 5/2013 | Dantanarayana | A61B 5/0876 |
| | | | 128/203.11 |
| 1,081,745 A1 | 12/2013 | Johnston et al. | |
| 1,192,186 A1 | 7/2016 | Greene | |
| 2002/0014241 A1 * | 2/2002 | Gradon | A61M 16/06 |
| | | | 128/205.25 |
| 2002/0043265 A1 * | 4/2002 | Barnett | A61M 16/06 |
| | | | 128/206.24 |
| 2002/0094473 A1 * | 7/2002 | Lin | H01M 2/1205 |
| | | | 429/86 |
| 2002/0162558 A1 | 11/2002 | Noble | |

(56) References Cited

U.S. PATENT DOCUMENTS

| | | | |
|---|---|---|---|
| 2002/0174868 A1 | 11/2002 | Kwok et al. | |
| 2002/0192525 A1 | 12/2002 | Neutzler | |
| 2003/0005931 A1* | 1/2003 | Jaffre | A61M 16/08 128/204.18 |
| 2003/0037788 A1* | 2/2003 | Gallem | A61M 16/08 128/206.21 |
| 2003/0079751 A1 | 5/2003 | Kwok | |
| 2003/0116160 A1 | 6/2003 | Kwok | |
| 2003/0127100 A1* | 7/2003 | Hollis | A61M 16/208 128/205.24 |
| 2003/0164170 A1* | 9/2003 | Drew | A61M 16/06 128/204.18 |
| 2003/0172936 A1 | 9/2003 | Wilkie et al. | |
| 2004/0065327 A1 | 4/2004 | Gradon et al. | |
| 2004/0065330 A1 | 4/2004 | Landis | |
| 2004/0094157 A1* | 5/2004 | Dantanarayana | A61B 5/0876 128/206.21 |
| 2004/0182397 A1 | 9/2004 | Wood | |
| 2004/0226566 A1* | 11/2004 | Gunaratnam | A61M 16/0666 128/207.18 |
| 2004/0261797 A1 | 12/2004 | White | |
| 2005/0011524 A1 | 1/2005 | Thomlinson | |
| 2005/0022828 A1* | 2/2005 | Fukunaga | A61M 16/1055 128/204.18 |
| 2005/0028821 A1 | 2/2005 | Wood | |
| 2005/0028822 A1 | 2/2005 | Sleeper | |
| 2005/0051177 A1 | 3/2005 | Wood | |
| 2005/0076913 A1* | 4/2005 | Ho | A61M 16/06 128/206.27 |
| 2005/0092326 A1 | 5/2005 | Drew et al. | |
| 2005/0199242 A1 | 9/2005 | Matula | |
| 2005/0241644 A1 | 11/2005 | Gunaratnam et al. | |
| 2006/0196509 A1 | 9/2006 | Drew et al. | |
| 2006/0266361 A1* | 11/2006 | Hernandez | A61M 16/06 128/206.11 |
| 2011/0041855 A1 | 2/2011 | Gunaratnam et al. | |

FOREIGN PATENT DOCUMENTS

| | | |
|---|---|---|
| AU | 95/16178 B | 7/1995 |
| AU | 9459430 | 2/1996 |
| AU | A 32914/95 | 2/1996 |
| AU | A 41018/97 | 4/1998 |
| AU | A 89312/98 | 1/1999 |
| AU | 712236 | 4/1999 |
| CA | 1039144 | 9/1978 |
| DE | 459104 | 4/1928 |
| DE | 701 690 | 1/1941 |
| DE | 159396 | 6/1981 |
| DE | 3015279 A1 | 10/1981 |
| DE | 3345067 A1 | 6/1984 |
| DE | 3537507 A1 | 4/1987 |
| DE | 3539073 A1 | 5/1987 |
| DE | 4004157 C1 | 4/1991 |
| DE | 4343205 A1 | 6/1995 |
| DE | 197 35 359 | 1/1998 |
| DE | 297 23 101 | 7/1998 |
| DE | 298 10846 U1 | 8/1998 |
| EP | 0 054 154 | 10/1981 |
| EP | 0 252 052 A1 | 7/1986 |
| EP | 0 264 772 A1 | 4/1988 |
| EP | 0 386 605 A1 | 2/1990 |
| EP | 0427474 A2 | 5/1991 |
| EP | 0 462 701 A1 | 12/1991 |
| EP | 0 602 424 | 11/1993 |
| EP | 0601708 | 6/1994 |
| EP | 0 608 684 A1 | 8/1994 |
| EP | 0 658 356 | 6/1995 |
| EP | 0 697 225 | 7/1995 |
| EP | 0697 225 A2 | 7/1995 |
| EP | 0 697 225 | 2/1996 |
| EP | 178 925 A2 | 4/1996 |
| EP | 0 747 078 A2 | 12/1996 |
| EP | 0 821 978 | 2/1998 |
| EP | 1 027 905 A | 8/2000 |
| EP | 1 057 494 | 12/2000 |
| EP | 1163923 A2 | 6/2001 |
| FR | 2 574 657 A1 | 6/1986 |
| FR | 2 658 725 A1 | 8/1991 |
| FR | 2 749 176 | 12/1997 |
| GB | 1395391 | 5/1975 |
| GB | 1 467 828 | 3/1977 |
| GB | 2 106 396 | 4/1983 |
| GB | 2145335 A | 3/1985 |
| GB | 2147506 A | 5/1985 |
| GB | 2 164 569 A | 3/1986 |
| GB | 2 236 681 A | 4/1991 |
| GB | 2 267 648 A | 12/1993 |
| JP | 463702 | 5/1971 |
| JP | 463703 | 6/1971 |
| JP | 57-1477 | 11/1982 |
| JP | 63105772 | 5/1988 |
| JP | 2-141775 | 11/1990 |
| JP | 7000521 | 1/1995 |
| JP | 9010311 | 1/1997 |
| JP | 09/216240 A | 8/1997 |
| JP | A-11-267234 | 10/1999 |
| JP | A-2000-140587 | 5/2000 |
| JP | 2001-511035 | 8/2001 |
| JP | 2001-333982 | 12/2001 |
| JP | 2002-95751 | 4/2002 |
| JP | 2004-570 | 1/2004 |
| JP | 2004-535226 | 11/2004 |
| WO | WO 80/01044 | 5/1980 |
| WO | WO 82/03548 | 10/1982 |
| WO | WO 84/001293 | 4/1984 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/39206 | 12/1996 |
| WO | WO 97/07847 | 3/1997 |
| WO | WO 97/41911 | 11/1997 |
| WO | WO 97/46281 | 12/1997 |
| WO | WO 98/04310 | 2/1998 |
| WO | WO 98/11930 | 3/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/34665 | 8/1998 |
| WO | WO 98/48878 | 11/1998 |
| WO | WO 99/004842 | 2/1999 |
| WO | WO 00/13751 | 3/2000 |
| WO | WO 00/74758 | 12/2000 |
| WO | WO 2001/026722 | 4/2001 |
| WO | WO 01/32250 | 5/2001 |
| WO | WO 01/89381 | 11/2001 |
| WO | WO 01/097892 | 12/2001 |
| WO | WO 02/096342 | 12/2002 |
| WO | WO 03/076020 | 9/2003 |
| WO | WO 2004/073778 | 9/2004 |
| WO | WO 2005/063328 | 7/2005 |
| WO | WO 2005/079726 | 9/2005 |

OTHER PUBLICATIONS

Roymech, "Fluid Flow in pipes", retrieved from http://www.roymech.co.uk/Related/Fluids/Fluids_Pipe.html.*

Wikipedia, "Borda-Carnot equation", retrieved from https://en.wikipedia.org/wiki/Borda%E2%80%93Carnot_equation.*

Neutrium, "Cavitation in Restriction Orifices and Valves", retrieved from https://neutrium.net/fluid_flow/cavitation-in-restriction-orifices.*

(56) References Cited

OTHER PUBLICATIONS

PCT International Search Report, PCT/AU2004/000207 (dated Apr. 28, 2004).
PCT International Search Report, PCT/AU2005/000515 (dated Jun. 2, 2005).
PCT International Preliminary Report on Patentability, PCT/AU2005/000515 (dated Oct. 11, 2006), 8 pgs.
U.S. Appl. No. 10/298,845, Kwok, filed Nov. 19, 2002.
U.S. Appl. No. 11/645,582, Kwok, filed Dec. 27, 2006.
Instruction Brochure for "E-vent-N" Aug. 1997, © Dräger Medizintechnik GmbH, 2 pages.
Translation of Official Action for Japanese Patent Application No. 2001-381410 dated Jun. 6, 2007 (2 pages).
Supplementary European Search Report issued in EP 05729503, dated Nov. 9, 2009.
Second Office Action issued in Chinese Appln. No. 200580012190.8, dated Feb. 5, 2010.
Office Action in Japanese Appln. No. 2004-197875 (dated Oct. 9, 2007) with English translation.
Examiner's First Report on Australian Patent Appln. No. 2005231520 (dated Mar. 31, 2010).
Japanese Office Action issued in JP Appln. No. 2001-381410 (dated Feb. 17, 2009) with English translation.
Office Action issued in related Japanese Appln. 2007-506619 (dated Oct. 19, 2010) with English translation.
Examination Report issued in related New Zealand Appln. No. 586208 (dated Jun. 22, 2010).
Office Action issued in related Japanese Appln. No. 2007-506619 (dated May 17, 2011).
Office Action issued in related Chinese Appln. No. 200910160819.3 (dated Jun. 30, 2011) with English translation.
Office Action issued in related Chinese Appln. No. 200910160820.6 (dated Aug. 3, 2011) with English translation.
Office Action issued in related Chinese Appln. No. 200910160819.3 (dated Apr. 18, 2012) with English translation.
Office Action issued in related Chinese Appln. No. 200910160820.6 (dated Jun. 18, 2012) with English translation.
Office Action issued in related Chinese Appln. No. 200910160820.6 (dated Sep. 29, 2012) with English translation.
Decision of Rejection issued in related Chinese Appln. No. 200910160820.6 (dated Jun. 18, 2013) with English translation.
Mask 1 Photographs, Respironics Inc., Reusable Full Mask (small) Part # 452033 Lot #951108.
Mask 2 Photographs, Puritan—Bennett, Adam Curcuit , Shell Part # 231700, Swivel Part # 616329-00, Pillows (medium) Part #616324.
Mask 3, Photographs, DeVilbiss Healthcare Inc., DeVilbiss Seal-Ring and CPAP Mask Kit (medium), Part 73510-669.
Mask 4 Photographs, Respironics Inc., Monarch Mini Mask with Pressure Port. Part # 572004, Monarch Headgear, Part # 572011.
Mask 5 Photographs, Healthdyne Technologies, Nasal CPAP Mask (medium narrow), Part # 702510.
Mask 6 Photographs, Healthdyne Technologies, Soft Series Nasal CPAP Mask, Part # 702020.
Mask 7 Photographs, DeVilbiss Healthcare Inc., Small Mask and Seal Rings, Part # 73510-668.
Mask 8 Photographs, Respironics Inc., Reusable Contour Mask (medium), Part # 302180.
Mask 9 Photographs, Healthdyne Technologies, Healthdyne Large Headgear.
Mask 10 Photographs, Respironics Inc., Soft Cap (medium), Part # 302142.
Mask 11 Photographs, Weinmann: Hamburg, Nasalmaskensystem mit Schalldämpfer (medium), Part # WN 23105.
Mask 12 Photographs, Life Care.
Mask 13 Photographs, Healthdyne Technologies.
Mask 14 Photograph, King System.
Mask 15 Photographs, Respironics Inc., Paediatric Mask.
Mask 16 Photographs, Hans Rudolph Inc., Hans Rudolph Silicone Rubber Face Mask/8900.
Office Action dated Feb. 15, 2017 issued in European Application No. 05729503.2 (8 pages).
Office Action dated Nov. 23, 2017 issued in European Application No. 05729503.2 (6 pages).

* cited by examiner

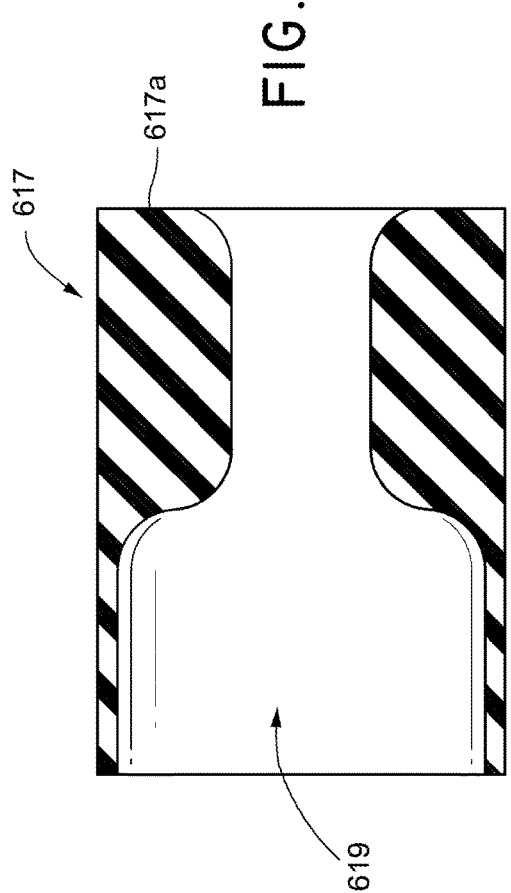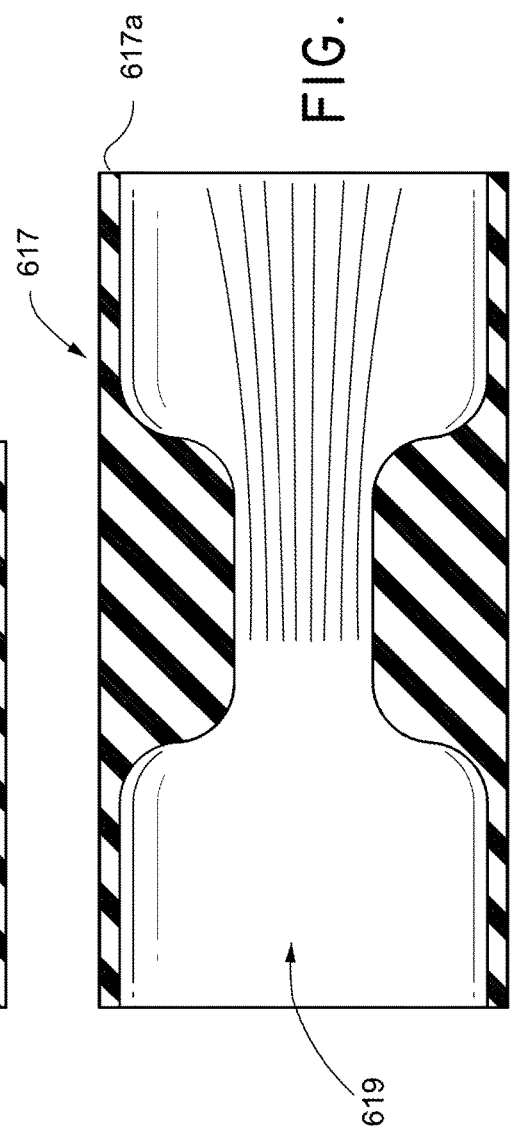

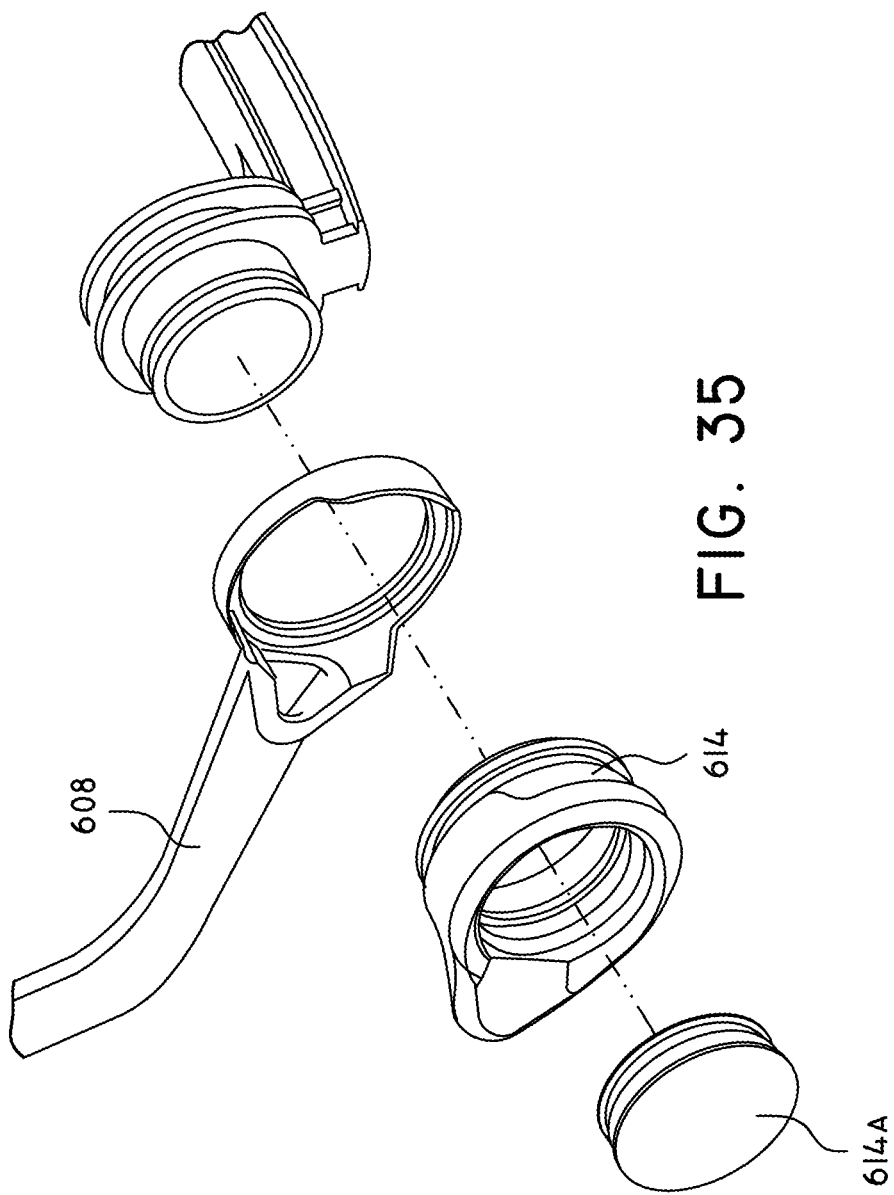

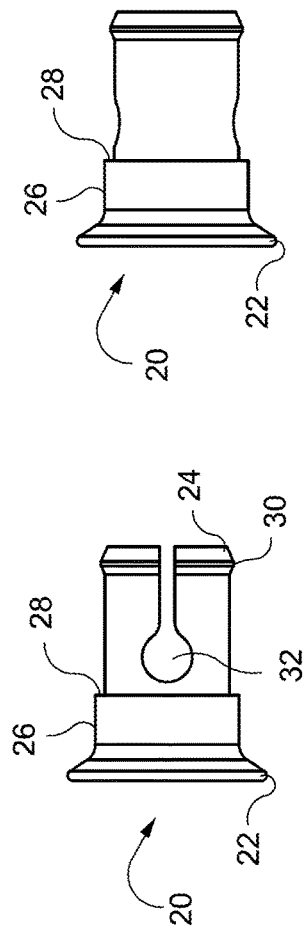
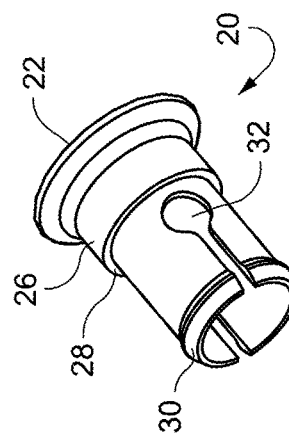
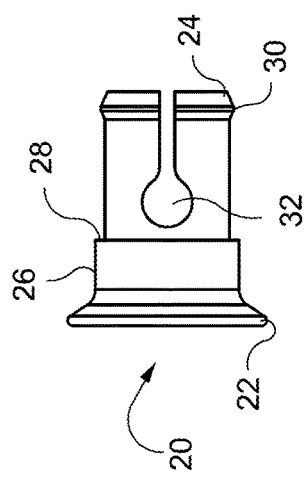
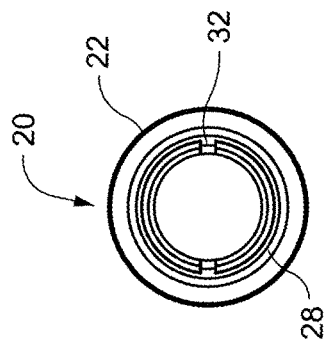
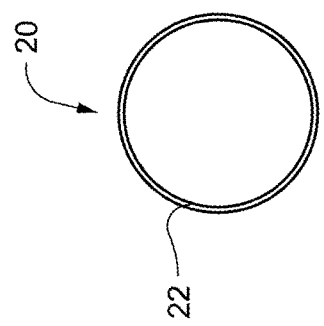
FIG. 38
FIG. 40
FIG. 37
FIG. 39
FIG. 36

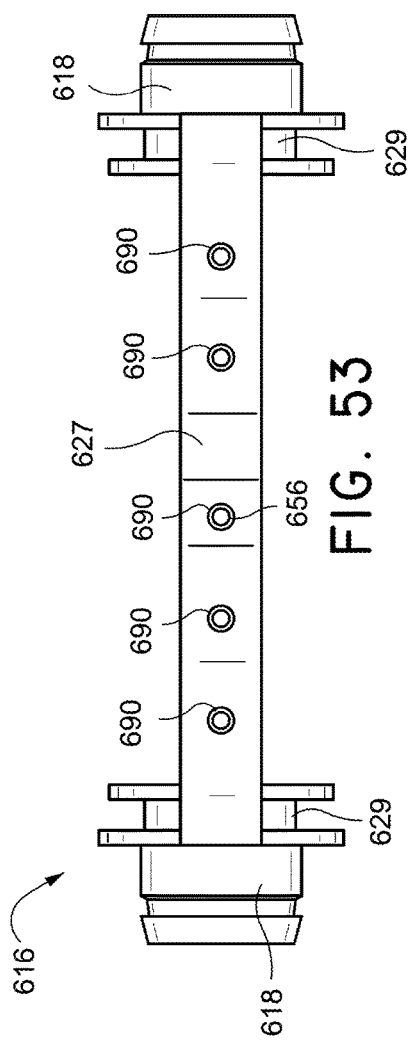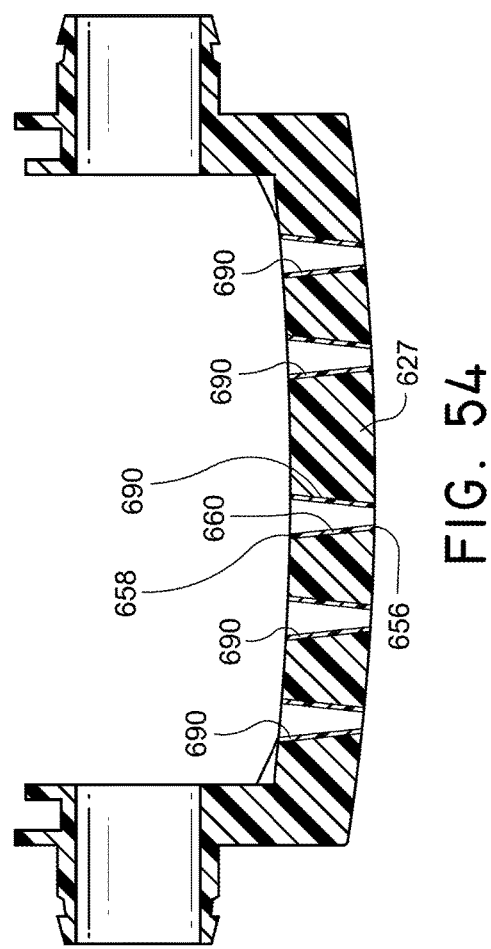

NASAL ASSEMBLY

CROSS-REFERENCE TO APPLICATIONS

This application is a continuation of U.S. patent application Ser. No. 12/926,213, filed Nov. 2, 2010, now U.S. Pat. No. 8,757,162, which is a continuation of U.S. patent application Ser. No. 11/101,657, filed Apr. 8, 2005, now U.S. Pat. No. 7,942,150, which claims the benefit of U.S. Provisional Application Nos. 60/560,610, filed Apr. 9, 2004, and 60/632,193, filed Dec. 2, 2004, each of which is incorporated herein by reference in its entirety.

FIELD OF THE INVENTION

The present invention relates to a nasal assembly used for treatment, e.g., of Sleep Disordered Breathing (SDB) with Continuous Positive Airway Pressure (CPAP) or Non-invasive Positive Pressure Ventilation (NPPV).

BACKGROUND OF THE INVENTION

Some nasal assemblies used in the treatment of SDB are designed for insertion into the nasal passages of the patient. Air or other breathable gas is supplied by a blower and passed along a flexible conduit to the nasal assembly.

The nasal assembly generally includes a relatively rigid shell, e.g., a frame, and a pair of nozzles (which may be in the form of nasal pillows, nasal prongs, cannula, or nasal puffs) that are mounted on the rigid shell and structured to be inserted into the nasal passages of the patient. The nozzles are usually held in place using a headgear assembly, the relatively rigid shell and headgear assembly being joined using some form of connector.

One form of known nasal assembly is described in U.S. Pat. No. 4,782,832 (Trimble et al.). Trimble discloses a nasal puff assembly 20 that includes a nasal puff 22 adapted to be worn adjacent the nose of a patient, together with a harness assembly 24 adapted to be worn over the head of the patient. The harness assembly 24 is designed to operatively hold puff 22 adjacent and partially within the nasal passages of the patient.

The puff 22 is in the form of a generally Y-shaped rigid hollow plenum chamber 28 together with a pair of laterally spaced apart nares elements 30. Adjustability of the nares elements 30 may be provided by rotatably mounting the elements 30 to the plenum chamber 28 and mounting the elements 30 in slots permitting selective lateral positioning of the elements 30 with respect to each other. Also, the harness assembly 24 may be adjusted to adjust the fit and seal of the nares elements 30 during use. That is, the force required to maintain a sufficient seal is directly associated with the force required to maintain a desired fit. Thus, adjustment of the fit or stability of the nasal assembly directly affects the seal, which can adversely affect patient comfort.

Other examples of nasal pillows or cannula mounted to rigid shells are disclosed in U.S. Pat. Nos. 5,724,965 and 6,431,172.

A nasal mask assembly manufactured by Viasys, i.e., Spiritus, includes a plenum chamber with a pair of adjacent or laterally spaced nares elements. A harness assembly is engaged with the plenum chamber to adjust the fit and seal of the nares elements during use. Similar to Trimble, adjustment of the fit or stability of the nasal assembly directly affects the seal, which can adversely affect patient comfort.

A nasal mask assembly manufactured by InnoMed, i.e., Nasal Aire, includes a plenum chamber with a pair of adjacent or laterally spaced nares elements. The nares elements are structured to engage within the mucosal surfaces or internal passages of the patient's nose to maintain the nasal mask assembly on the patient's face and to provide a seal. See, e.g., U.S. Pat. No. 5,533,506.

A nasal mask assembly manufactured by Stevenson Industries (see U.S. Pat. No. 6,012,455), i.e., CPAP-Pro, includes a dental anchor, a platform, and air supply tubes having nasal pads, wherein the platform supports the air supply tubes. The dental anchor is sized to be engaged between the teeth in the patient's mouth so as to retain the assembly in place.

PCT Application Publication No. WO 00/13751 discloses a device that includes gas delivery elements positioned into engagement with the patient's nose by a mouthpiece fitted to the patient's teeth.

A common problem with known nasal assemblies, such as those discussed above, is patient comfort. For example, the prongs tend to irritate the patient's nose due to the tension applied by the headgear assembly that pulls the rigid shell and prongs towards the patient's nose.

Another problem is achievement of a sealing fit with the patient's nasal passages without sacrificing patient comfort.

Another problem is irritation of the inside of the patient's nostrils caused by contact with the prongs, e.g., an edge thereof.

Another problem is irritation of the inside of the patient's nostrils caused by air jetting (air flow irritation) from the prongs.

Another problem is adjustment of the nasal assemblies relative to the nose and/or head of the patient so as to accommodate various shapes and angles of patient's noses.

Still another problem is the direct association between sealing and stability forces that can affect patient comfort.

SUMMARY OF THE INVENTION

One aspect of the invention is directed towards a nasal assembly that provides more comfort to the patient.

Another aspect of the invention is directed towards a nasal assembly that provides an effective seal with the patient's nasal passages. Preferably, the nasal assembly is a nozzle assembly including nozzles which comfortably come into contact with the external rim of the nares and avoid the sensitive internal passages (e.g., mucosal surfaces or internal passages) of the nasal passage.

Still another aspect of the invention is directed towards a nasal assembly that does not rely on tension from the headgear assembly to provide an effective seal between the nozzles and the patient's nasal passages.

Still another aspect of the invention is directed towards a nasal assembly that is unobtrusive.

Still another aspect of the invention is directed towards a nasal assembly that is easy to use.

Still another aspect of the invention is directed towards a nasal assembly that maintains a headgear adjustment setting.

Another aspect is to provide a vent having a profile that is configured to provide improved performance.

Still another aspect of the invention is directed towards a nasal assembly that helps decouple sealing and stability forces. Specifically, one aspect of the invention is directed towards a nasal assembly that is structured such that the stability forces that act to maintain the nasal assembly on the patient's face are separated or at least better distinguished from the sealing forces that act to maintain a seal between the nasal assembly and the patient's face.

Yet another aspect of the invention is directed towards a nasal assembly that provides a greater range of movement for nozzles of the nasal assembly.

Another aspect of the invention provides a nasal assembly for delivering breathable gas to a patient. The nasal assembly includes a frame having a main body and a side frame member provided on each lateral side of the main body, each side frame member including an integrally formed first connector portion. A nozzle assembly includes a gusset or base portion and a pair of nozzles. The nozzle assembly is coupled with the main body of the frame with the pair of nozzles structured to sealingly engage with nasal passages of a patient's nose in use. A pair of inlet conduits are structured to deliver breathable gas into the frame and nozzle assembly for breathing by the patient. A pair of second connector portions are removably and rotatably connected to respective first connector portions of the frame. The second connector portions are in communication with the inlet conduits via angle connectors. A headgear assembly is removably connected to at least one of the second connector portions and the angle connectors so as to maintain the frame and the nozzle assembly in a desired adjusted position on the patient's face.

In accordance with yet another aspect, a nasal assembly for delivering breathable gas to a patient comprises a frame having a main body and a side frame member provided on each lateral side of the main body; a patient interface provided to the main body of the frame; an elbow structured to deliver breathable gas into the frame and patient interface for breathing by the patient, the elbow being structured to be removably connected to each lateral side of the frame; and a plug structured to be removably connected to each lateral side of the frame. The positions of the plug and elbow may be selectively interchanged.

Still another aspect is to provide a nasal assembly including a baffle provided to the frame.

Yet another aspect of the invention is to provide a nasal assembly including a vent provided to the frame that allows for the exit of exhaled gas.

Other aspects, features and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 4 and 5 illustrate cross-sectional views of a vent aperture according to the present invention;

FIGS. 32-35 illustrate still another embodiment of the present invention;

FIGS. 36-41 illustrate a plug in accordance with an embodiment of the present invention;

FIGS. 43-45A and 45C-45H illustrate vents in accordance with further embodiments of the present invention;

FIG. 45B illustrates a prior art vent;

FIGS. 52-54 illustrate a frame according to an embodiment of the invention; and

DETAILED DESCRIPTION OF ILLUSTRATED EMBODIMENTS

The following includes descriptions of several illustrated embodiments of the present invention. Each illustrated embodiment includes features that may be used with and/or in the other embodiments, or with the embodiments and/or components described in U.S. Non-Provisional application Ser. No. 10/781,929, as would be apparent to those of ordinary skill in the art.

Figure 1:
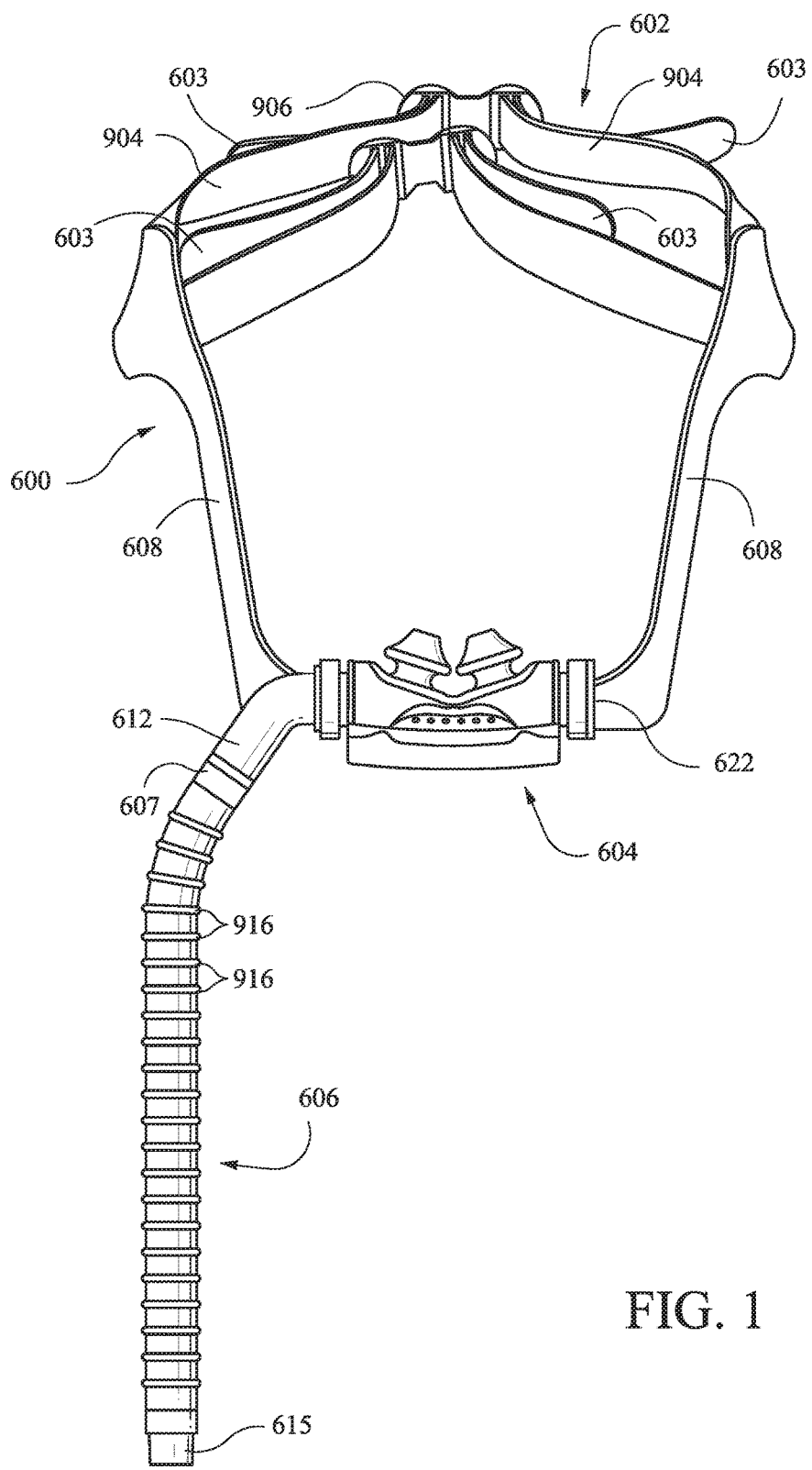
FIG. 1 is a perspective view of yet another embodiment of a nasal assembly.

FIGS. 1-13 illustrate another preferred embodiment of the present invention. As shown in FIG. 1, a mask assembly 600 includes headgear 602 and a cushion assembly 604 (also referred to as a nozzle assembly). Headgear 602 is designed to capture the crown of the patient's head. Adjustment of strap tension can be accomplished by pulling loose tabs 603 on the top of the head in opposite directions. The pulling direction is not aligned with the force the nozzle assembly applies to the patient. Therefore, the patient is more isolated from the strap adjustment forces. Yokes provide stability to the sides. Yokes 608 retain at least a partial portion of the basic shape of headgear, which facilitates donning of the headgear. Headgear need not include adjustability toward front of the face, as all adjustment of headgear can be effected at the back or top of the head.

In the embodiment of FIG. 1, one end of the cushion assembly 604 is provided with a plug 622 and the other end is provided with a swivel elbow 612. The positions of the swivel elbow 612 and the plug 622 may be interchanged, according to preference, e.g., the typical sleeping position of the patient. An air delivery tube 606 is joined to the swivel elbow 612. The air delivery tube 606 may include a swivel connector 607 and includes an end 615 which also may be provided with a swivel connector. The end 615 is provided with a source of pressurized gas.

As shown in FIG. 1, the elbow 612 is angled about 120° from the cushion assembly 604. This helps to keep the tube out of line of sight, to minimize pressure drop and to maintain the flexion point of tube as close to the face as possible. However, the elbow may have a typical 90° bend as shown, e.g., in FIGS. 2 and 3.

Figure 2:
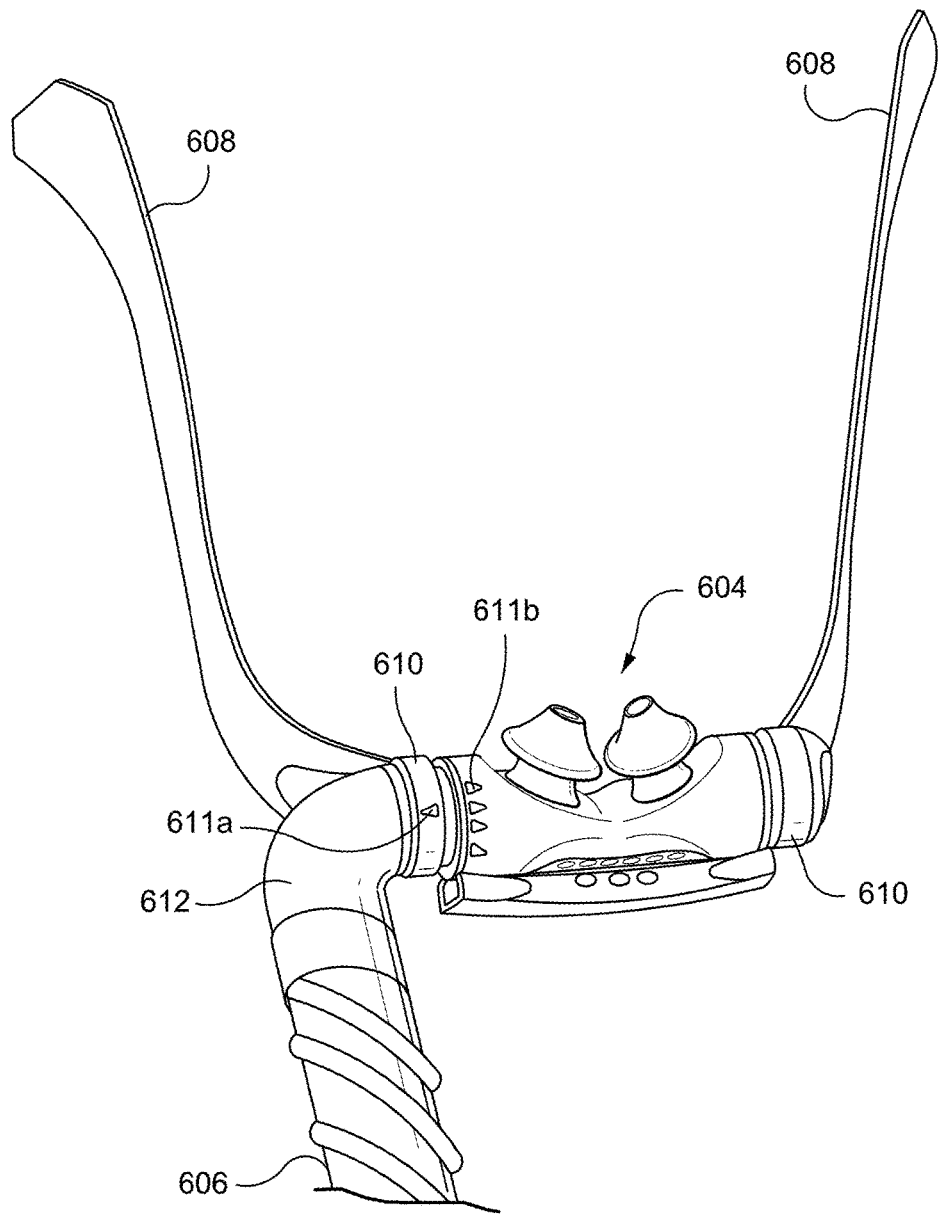
FIG. 2 is an isometric view illustrating a portion of the nasal assembly shown in FIG. 1.

FIG. 2 is a schematic perspective view of the mask assembly 600 shown in FIG. 1, but only yokes 608 of headgear 602 are shown, without the straps, e.g., 904, etc. The yoke 608 may include a yoke ring 610. As shown in FIG. 2, the cushion assembly may be adjustably rotated with respect to headgear, to a position which best fits the patient. In FIG. 2, the ring 610 of the yoke 608 of the headgear includes an alignment marker 611a and the cushion includes a plurality of alignment markers 611b that can be selectively aligned with marker 611a.

Figure 3:
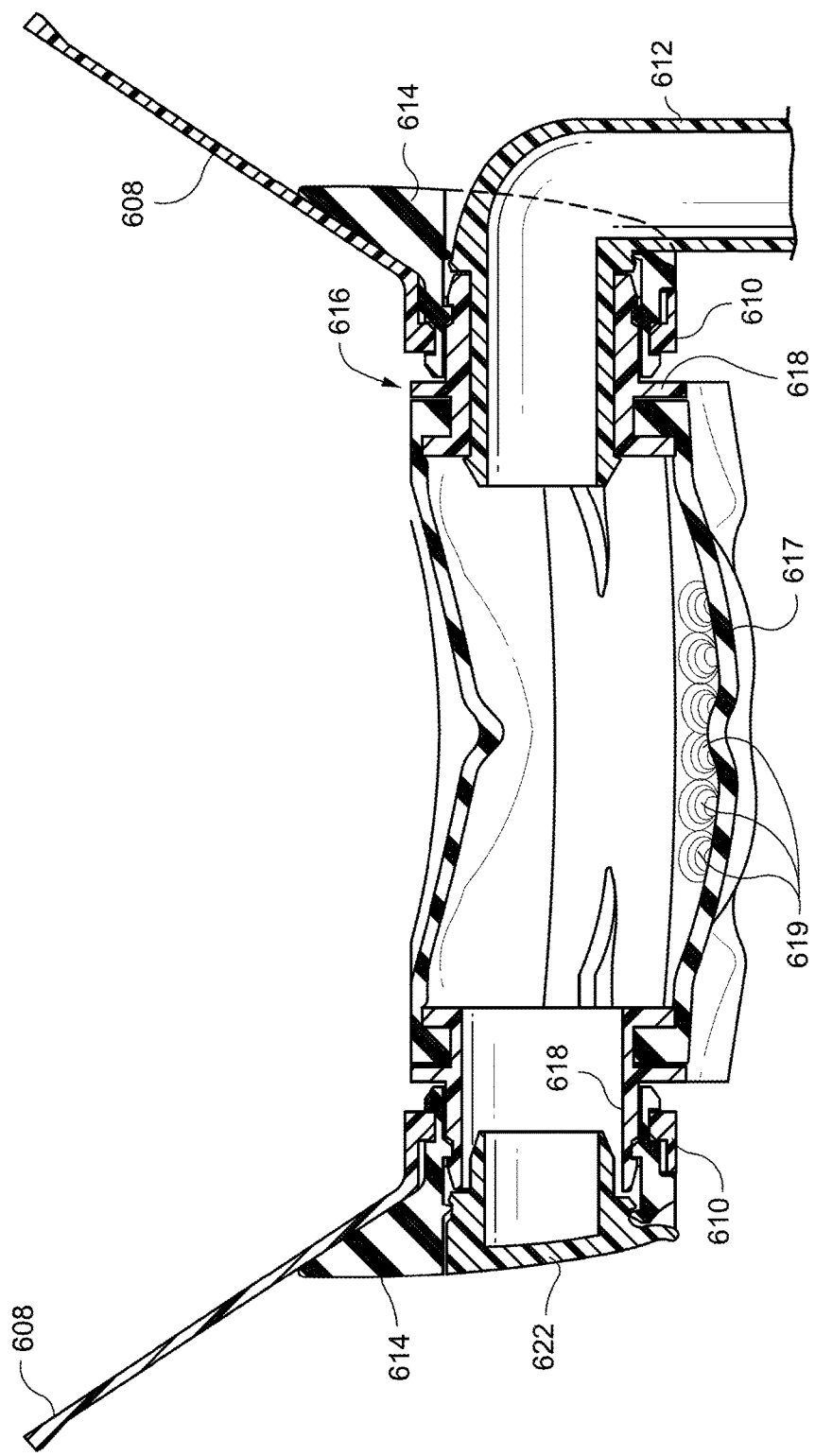
FIG. 3 is a cross-sectional view of a portion of a nasal assembly according to the present invention.

FIG. 3 is a cross-sectional view of a portion of the cushion assembly 604. In particular, the cushion assembly 604 includes a frame 616 which supports a cushion 617. The frame 616 includes a first connector portion 618 provided to each end of the frame 616 and/or cushion 617. Each first connector portion 618 is provided with or to a seal ring 614. Both seal ring and plug are examples of second connector portions that are connected or otherwise provided to the first connector portions 618. As seen in FIG. 3, the left hand side of the mask assembly includes the plug 622 while the right hand side of the mask assembly includes the swivel elbow 612, i.e., the reverse arrangement view shown in FIGS. 1 and 2.

FIG. 3 shows that the cushion 617 includes a plurality of vent apertures 619, each of which is designed to reduce noise. Cross-sections of two possible aperture profiles are shown in FIGS. 4 and 5. In FIG. 5, the end 617a displaces any potential noise creating flash (i.e., a molding seam) out of main air path through bore of vent. Stated differently, the molding seam is moved from a position from where it could potentially create noise, to a position where it is less likely to create noise.

Figure 6:
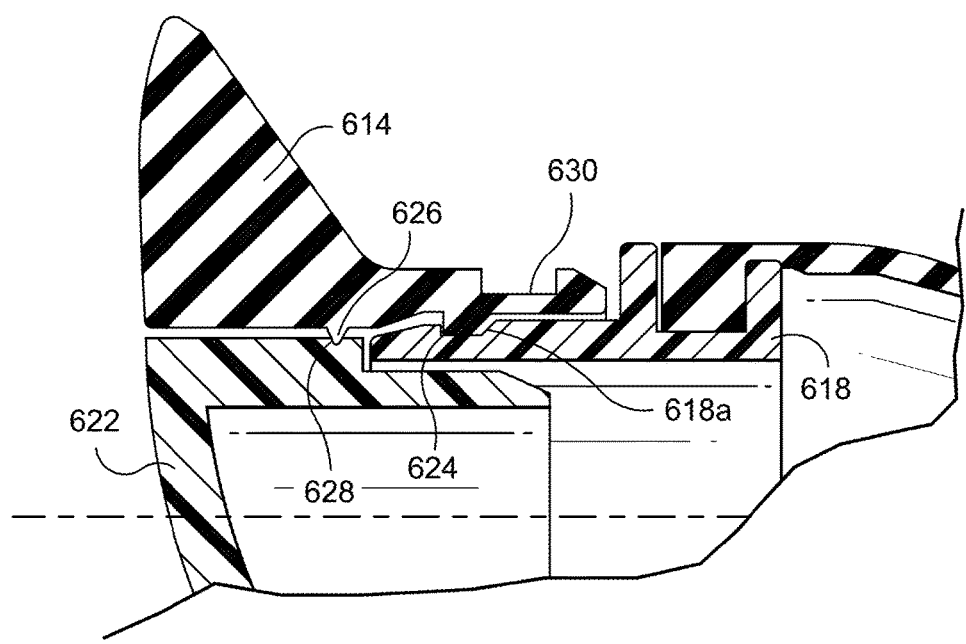
FIG. 6 is a partial enlarged cross-sectional view of the left hand side of FIG. 3.

FIG. 6 is a partial cross-sectional view showing the interaction between the seal ring 614, first connector portion 618 and the plug 622. In particular, the seal ring 614 may be provided with first and second protrusions 624, 626, respectively. The first protrusion 624 may interact with a groove 618a provided in the first connector portion 618, for sealing and/or locking purposes. The second protrusion 626 may interact with a groove 628 provided in the plug 622, the sealing and/or locking purposes. As shown in FIG. 6, each seal ring 614 includes a groove 630 to receive a respective one of the rings 610 of the yoke 608. In FIG. 6, the yoke 608 is not shown.

Figure 7:
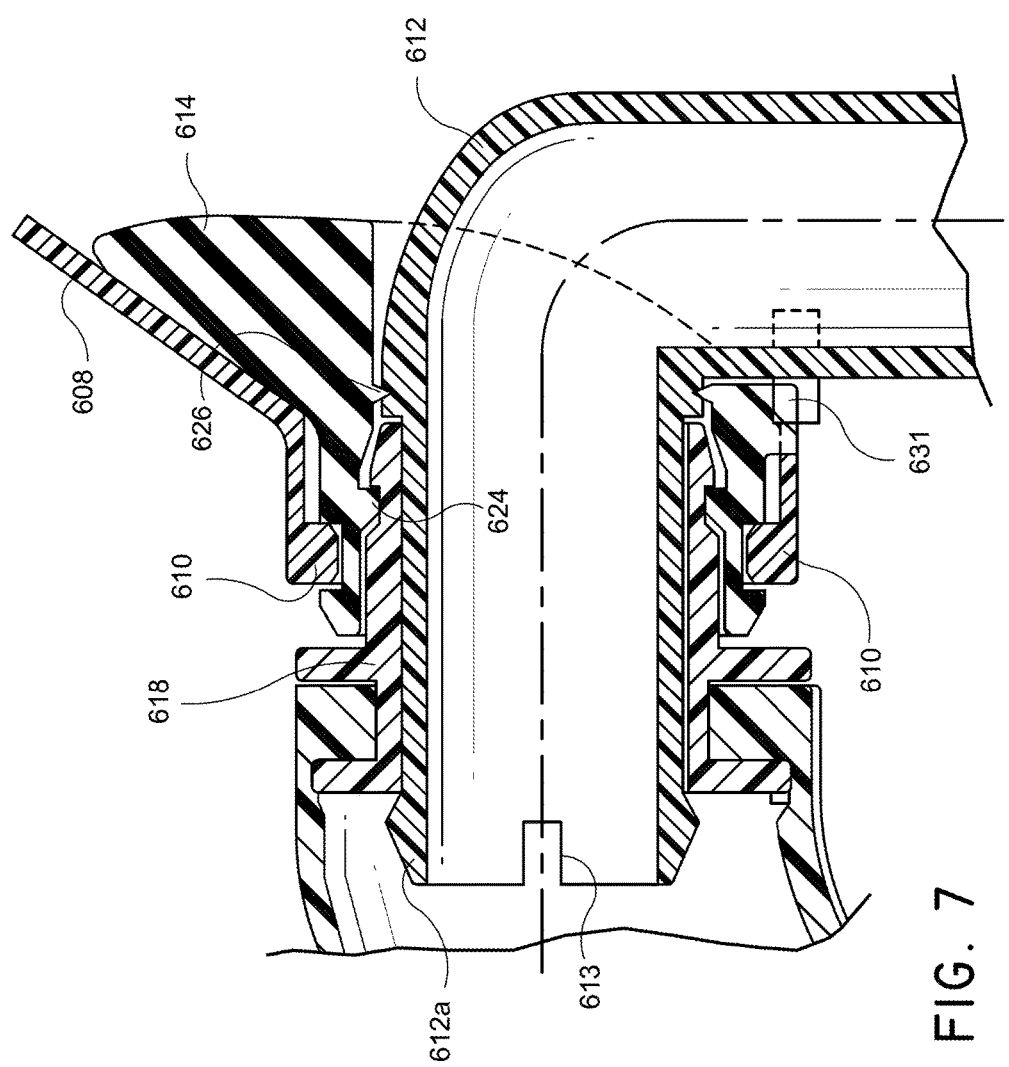
FIG. 7 is an partial enlarged cross-sectional view of the right hand side of FIG. 3.

FIG. 7 is an enlarged partial cross-sectional view of the mask assembly 600 on the right hand side of FIG. 3. A first end 612a of the swivel elbow 612 is inserted in and received within the first connector portion 618. The first end 612a may include an enlarged head portion which prevents inadvertent dislodgement of the swivel elbow 612 from the assembly. The front end 612a may include at least one slot 613 to allow the enlarged head portion to reduce its diameter upon insertion by resiliently flexing. Preferably, there are a plurality of such slots, e.g., four slots. The seal ring 614 may include first and second protrusions 624, 626, as described above. In this case, the second protrusion 626 may interact by friction with the outer circumference of the swivel elbow 612, and provide a seal. Moreover, the swivel elbow 612 may be provided with a groove or other structure to receive the second protrusion 626.

FIG. 7 also schematically shows that the swivel elbow 612 and the seal ring 614 may include a swivel stop 631. For example, the swivel stop 631 may be formed as part of the yoke 608.

Figure 8:
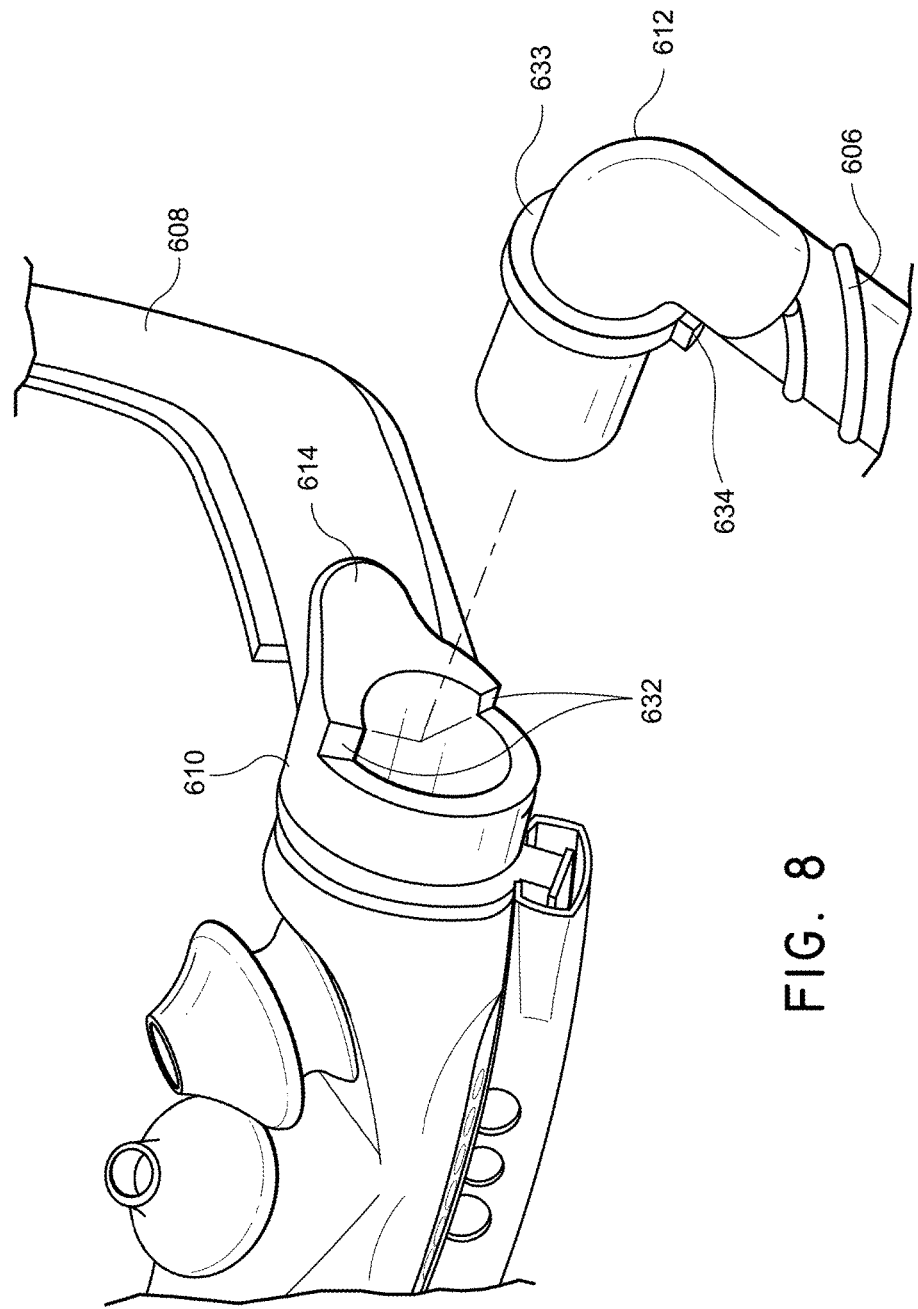
FIG. 8 is an exploded perspective view showing the interface between seal ring and elbow swivel according to an embodiment of the present invention.

Alternatively or in addition, as shown in FIG. 8, the swivel elbow 612 may be provided with a ring 633 including a protrusion 634. The seal ring 614 may be modified to include swivel stops 632. Accordingly, the protrusion 634 may rotate along with swivel elbow 612 until the protrusion 634 abuts against the swivel stop 632. Therefore, movement of the air delivery tube 606 can be confined with a predetermined range of movement, e.g., about 220°-300°, and preferably 250°-270°, thus minimizing or avoiding undesirable contact between the air delivery tube and the patient.

Figure 9:
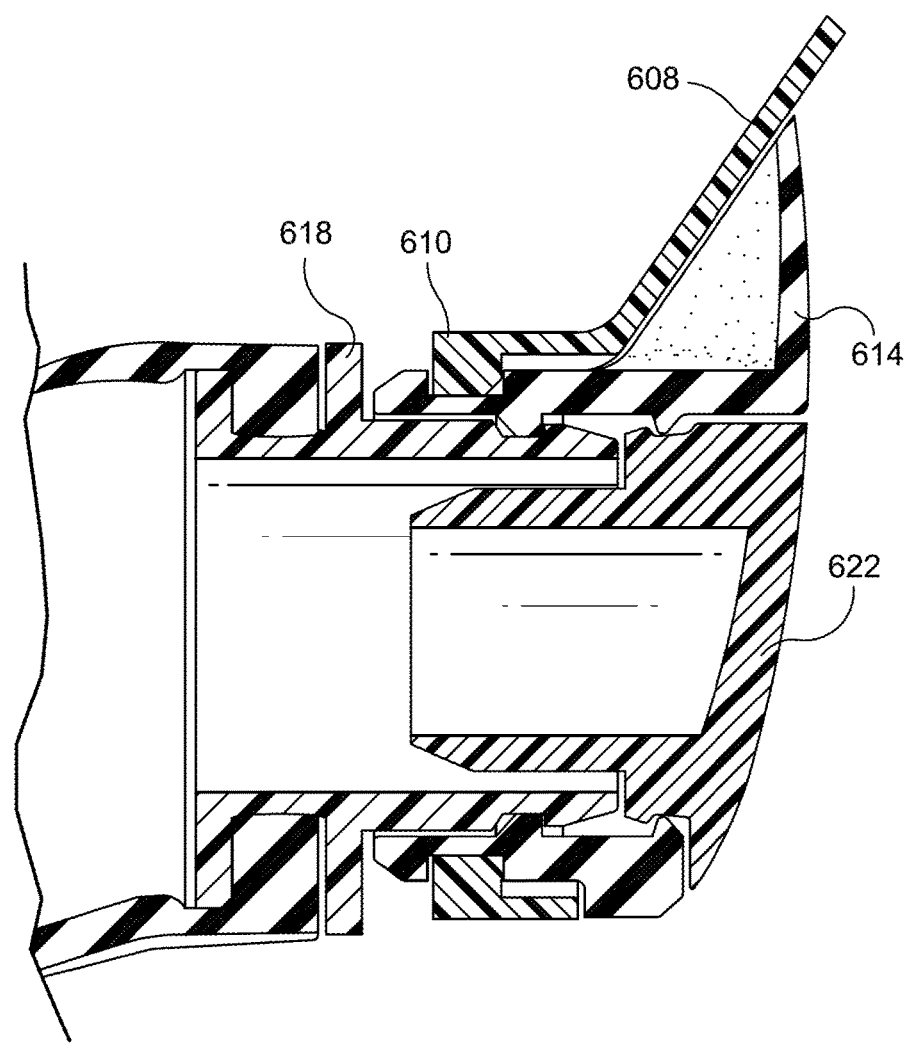
FIG. 9 is a partial cross-sectional view of a portion of the mask assembly shown in FIG. 1.

FIG. 9 is a partial cross-sectional view of the assembly of the frame, first connector portion 618, yoke 608, seal ring 614 and plug 622. FIG. 9 shows the plug 622 to be inserted in the right hand side of the cushion assembly 604, as shown in FIG. 1.

Figure 10:
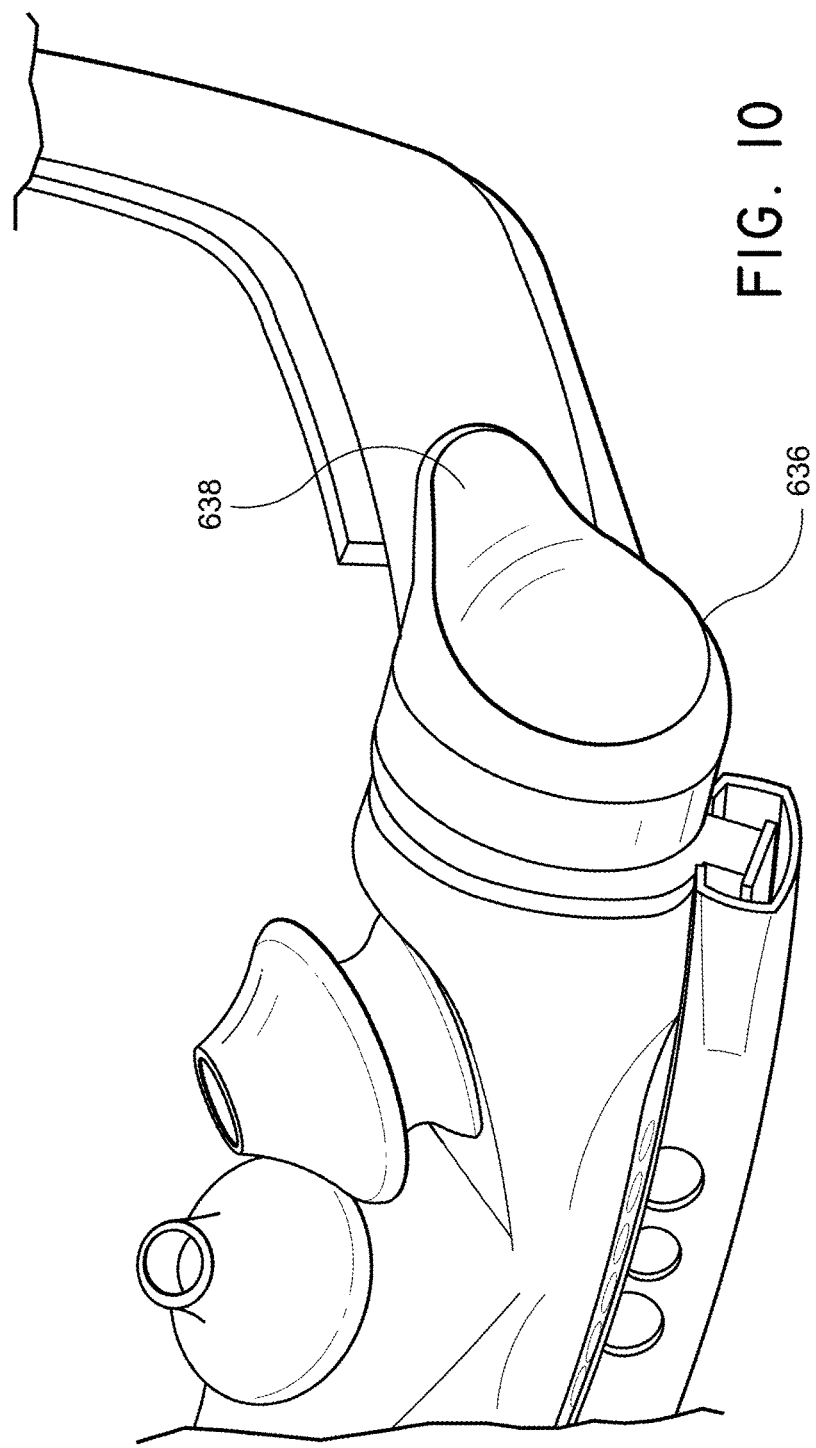
FIG. 10 illustrates still another embodiment of the present invention with an integral plug and seal assembly.

FIG. 10 shows an alternative embodiment of the invention in which the plug and seal ring are formed of a single integral piece. As shown in FIG. 10, the seal ring 636 includes a flange portion 638 which generally follows along a contour of the yoke 608. This is best shown in the cross-sectional view of FIG. 3 where the seal ring 614 and the yoke 608 are positioned closely adjacent one another.

These and other illustrated embodiments may provide for improved decoupling of the air delivery tube 606 and/or swivel elbow 612 from the cushion assembly 604. In addition, these and other embodiments provide a choice of tube routing, which can be either up or down or on the left or right hand sides of the cushion assembly 604. As such, these embodiments may be perceived as less obtrusive and is significantly lighter, and including relatively few parts, which facilitates manufacture, assembly and cleaning.

The swivel elbow 612 may be provided with a quick release mechanism (not shown). The swivel elbow 612, as shown in FIG. 7, is able to fit and snap into the mask frame 616. This construction allows free swiveling within the frame 616, between a range of defined angles, thereby ensuring that the tube does not get into an uncomfortable position with respect to the head and pillow.

The seal ring 614 is structured such that it cooperates with the geometry of the elbow swivel 612. In addition, the seal ring 614 may be connected to the ring 610 of the yoke 608. The seal ring 614 may be permanently connected to the ring 610, e.g., via co-molding. For example, the swivel stop 631 in FIG. 7 may be formed as part of the ring 610. The first connector portion 618 on each side of the frame 616 may be rotated with respect to the seal ring 614, to thereby position the cushion assembly 604 accordingly. The seal ring 614 seals the swivel elbow 612 preferably with minimum friction. Each seal ring 614 may accommodate either the plug 622 or the swivel elbow 612. The seal ring 614 is large enough for patients to handle, especially patients with reduced manual dexterity.

The plug 622 may be press fit into the seal ring 614. The plug 622 can also be designed to be press fit into the frame. The plug 622 may be made from hard polymer, for example, polypropylene. A recess (not shown) may be provided to remove the plug 622. The plug functions to seal the frame and cushion assembly on the side opposing the air delivery tube. The plug 622 is large enough for patients to handle, even with reduced manual dexterity.

The tubing 606 may be permanently attached to the end of the swivel elbow 612. However, a push-on friction connection may also be suitable. The tube length may be between 200 mm and 400 mm, preferably 250 and 350 mm, for example, or any other length which will not interfere with the patient's face.

As shown in FIGS. 7 and 8, respectively, the yokes 608 and seal ring 614 may be provided with structure to limit the angular or rotational movement of the swivel elbow 612 with respect to the first connector portion 618.

Further, the headgear and/or yoke may be provided with a tube retention feature to control the tube position. For example, simple VELCRO® straps may be provided along some portion of the headgear to restrain movement of the air delivery tube.

Figure 11:
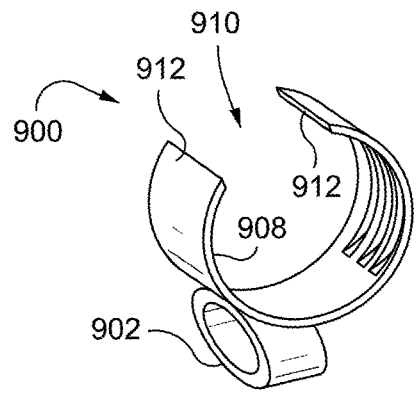
FIGS. 11 and 12 illustrate a tube retainer according to an embodiment of the present invention.
Figure 12:
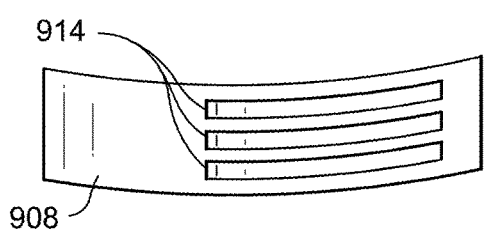

In the example shown in FIGS. 11 and 12, a tube retainer 900 includes a first portion 902 to be connected or attached to one of the straps of headgear. For example, the first portion 902 can be in the form of a loop that is attached to a portion 904 of headgear strap shown in FIG. 1. Attachment can be accomplished by threading the headgear strap 904 though the first portion 902 before the headgear strap 904 is threaded through the headgear buckle 906. The retainer 900 includes a second portion 908 provided or attached to the first portion 902. The second portion 908 may be made of a resilient plastic that retains the shape shown in FIG. 11, with a gap 910 defined between two ends 912 of the second portion 908. The gap 910 is sized to be smaller than the diameter of the air delivery tube 606, so as to reliably hold the tube 606. Alternatively, the second portion 908 can be a VELCRO® loop, with the ends 912 including the mating hooks and loops. As shown in FIGS. 11 and 12, the second portion may include one or more slots 914 to receive ribs 916 (FIG. 1) of the air delivery tube 606, to thereby prevent axial sliding of the tube 606. With this arrangement, the tube 606 can be reliably held in a position over the patient's head.

Figure 13:
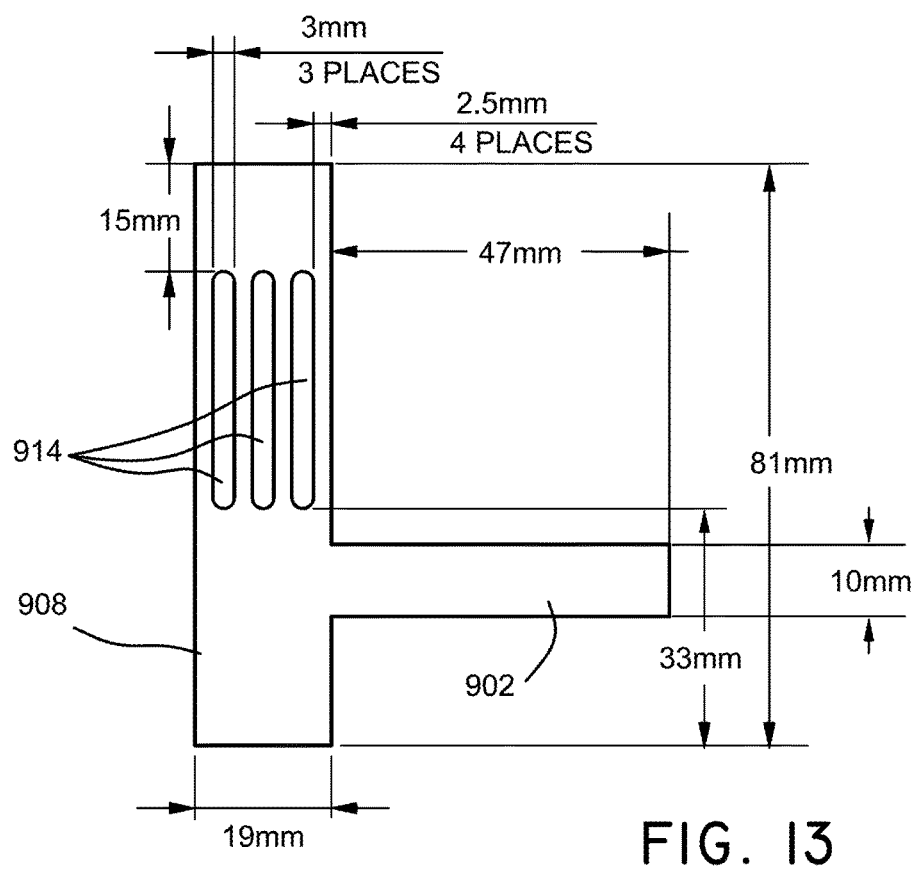
FIG. 13 illustrates another tube retainer according to an embodiment of the present invention.

FIG. 13 illustrates a plan view of a tube retainer, wherein like reference numbers relate to like parts. In FIG. 13, exemplary dimensions of the tube retainer are shown. It is to be noted that these dimensions are examples only, and the dimensions can be changed up to about ±20% of the values shown therein. In the embodiment of FIGS. 11-13, first portion 902 is optional as second portion 908 alone can affix the tube to the headgear.

Figure 14:
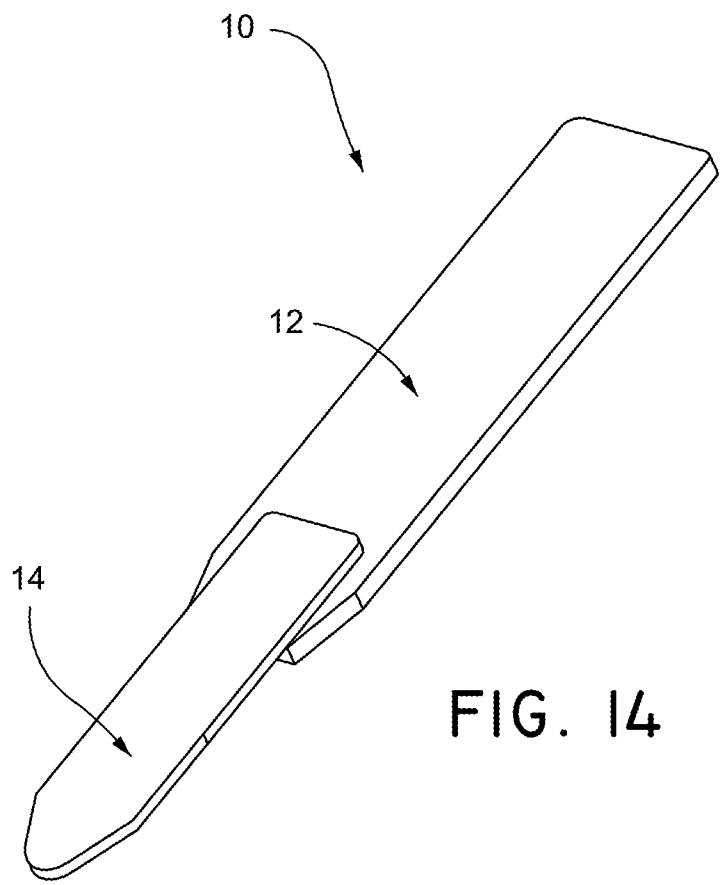
FIGS. 14-18 illustrate another tube retainer according to an embodiment of the present invention.
Figure 15:
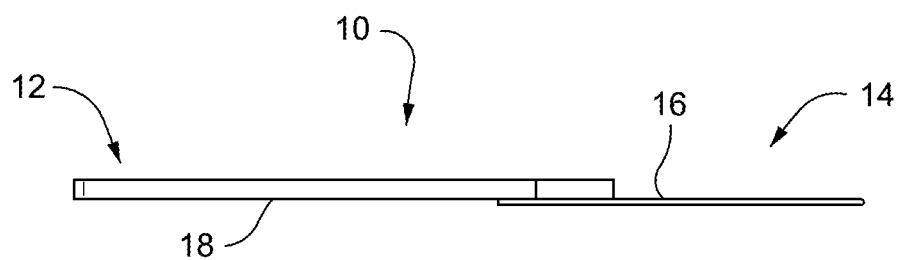

FIGS. 14-18 illustrate a retainer 10 according to yet another embodiment of the present invention. The retainer 10, as shown in FIG. 14, includes a main body 12 and a tab 14. The tab 14 includes hook-type fasteners on surface 16 while main body includes loop-type fasteners on surface 18, as shown in FIG. 15.

Figure 16:
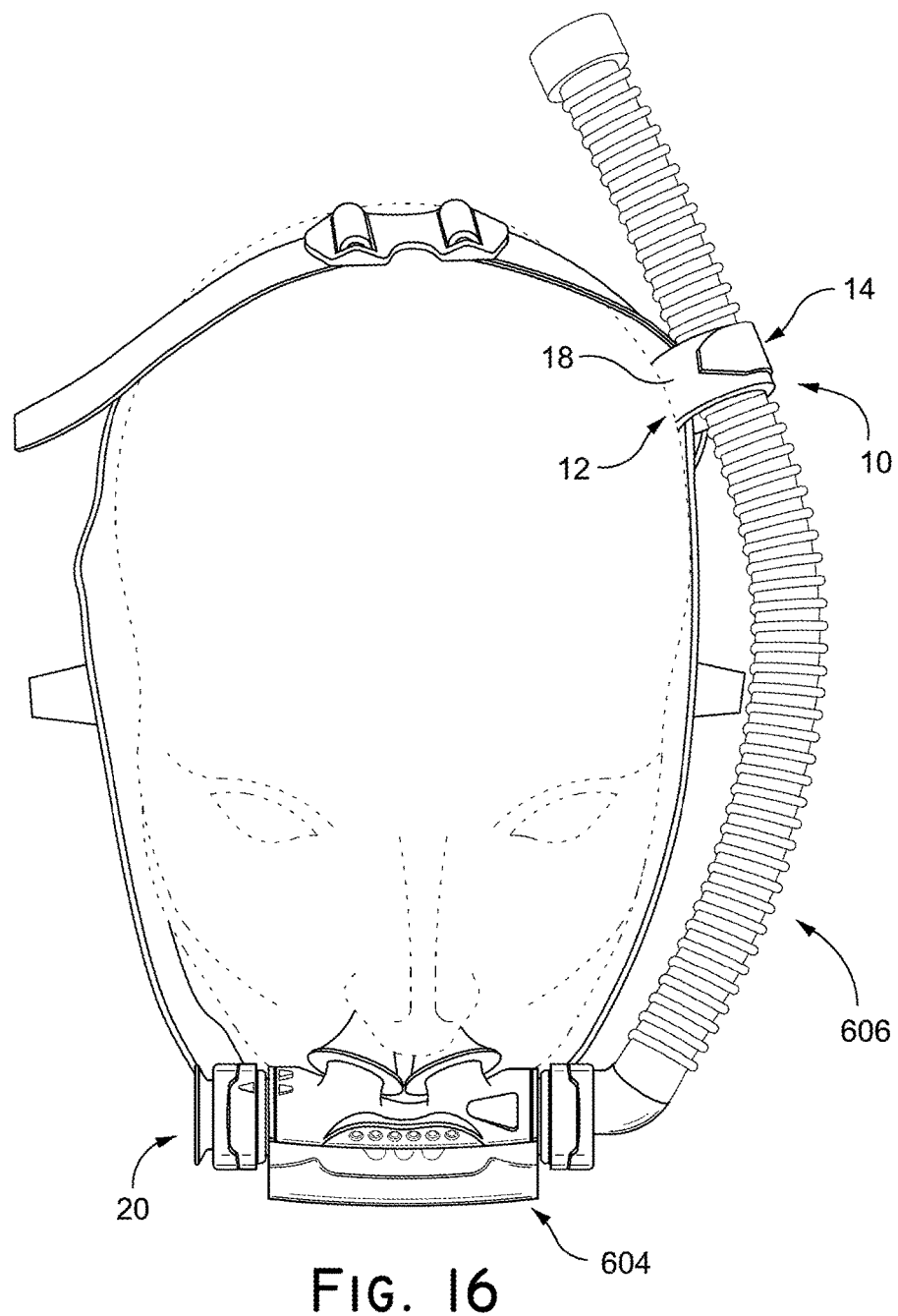
Figure 17:
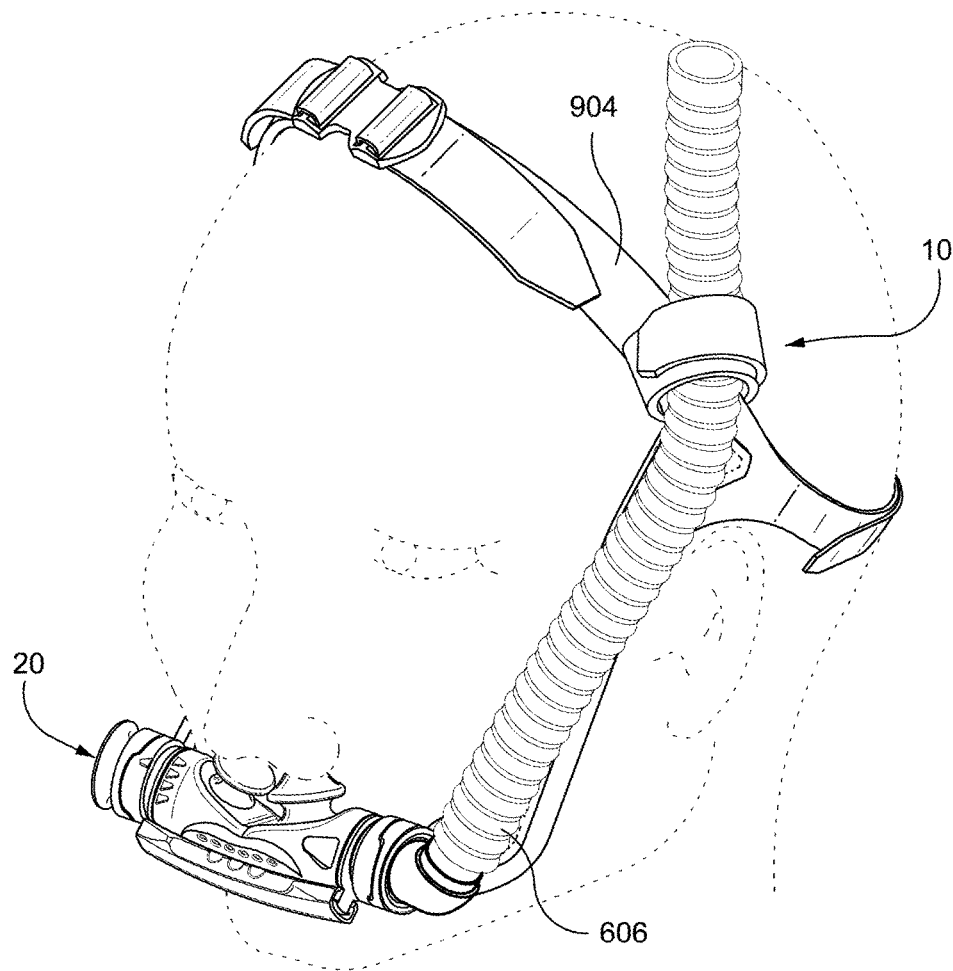
Figure 18:
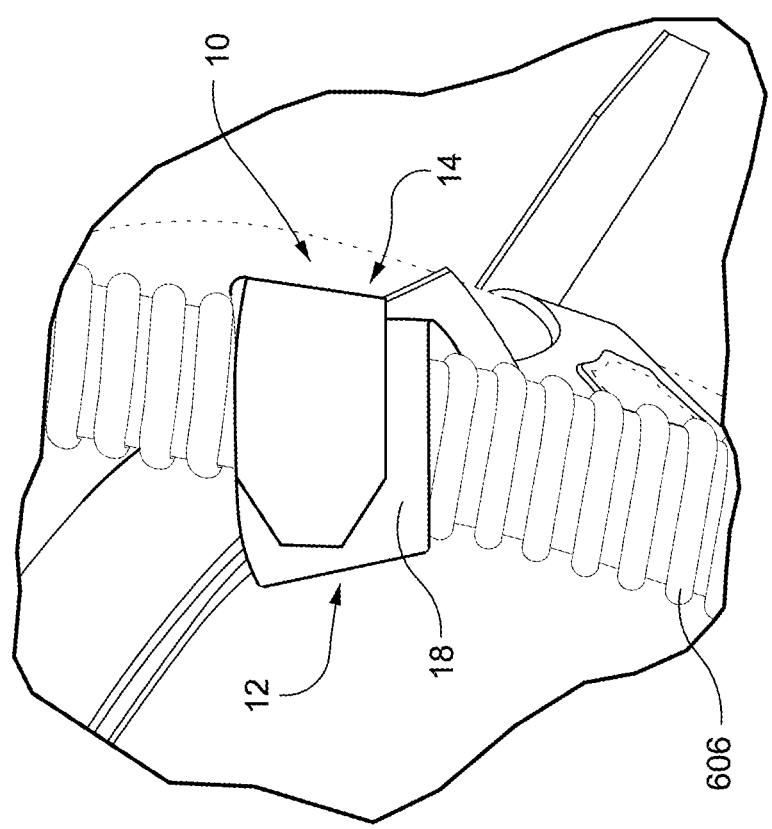

FIGS. 16-18 illustrate the positioning of the retainer 10 on a sample patient's head. As seen in FIGS. 16-18, the retainer 10 is provided to guide the air delivery tube 606 around the patient's head. The retainer 10 engages a portion of head strap 904 and is then wrapped around air delivery tube 606 with the hook and loop fasteners on surfaces 16 and 18 engaged.

Main body 12 of retainer 12 can be formed of any suitable material, such as a Breath-O-prene™. The Breath-O-prene™ may be provided with an underside fabric layer if desired for added comfort. All materials used in constructing retainer 10 are available from Accumed Technologies, Inc.

The nasal assemblies described above and below have several advantages. For example, the nasal assemblies are unobtrusive due to their small overall size and weight. The nasal assemblies provide a high level of comfort due to the minimal force applied to the patient's nose—and contact with the bridge can be eliminated. The nasal assemblies are easy to use and include minimal parts and adjustments, e.g., the inlet conduits can be easily adjusted to extend upwardly over the head of the patient or downwardly below the chin of the patient. The pressurized supply can be easily connected to and disconnected from the connectors without altering the headgear setting. Also, the nasal assemblies allow for greater nozzle range of motion to accommodate a wide range of patients. That is, the nozzles can be rotated with respect to the patient's face by rotating the frame relative to the headgear assembly. Further, strap tension need not be as high as the area of contact with the face is less. The headgear provides stability, e.g., the yokes help maintain the mask assembly's position on the face. The adjustment of the headgear is designed such that the force required to tighten the straps is not applied to the patient's face, e.g., the straps can be pulled in opposite directions above the head to counteract one another. It is relatively easy to find balance between performance and comfort. In addition, the weight, noise level, and/or number of parts of the mask assembly is reduced.

An Appendix including additional drawings and depictions of various aspects of preferred embodiments of the invention is included in U.S. Provisional Application No. 60/529,696, filed Dec. 16, 2003 and incorporated herein by reference in its entirety. To the extent that any drawing in the labeled Figures or the Appendix includes dimensions, those dimensions are exemplary only and may be changed without departing from the scope of the disclosure.

Figure 19:
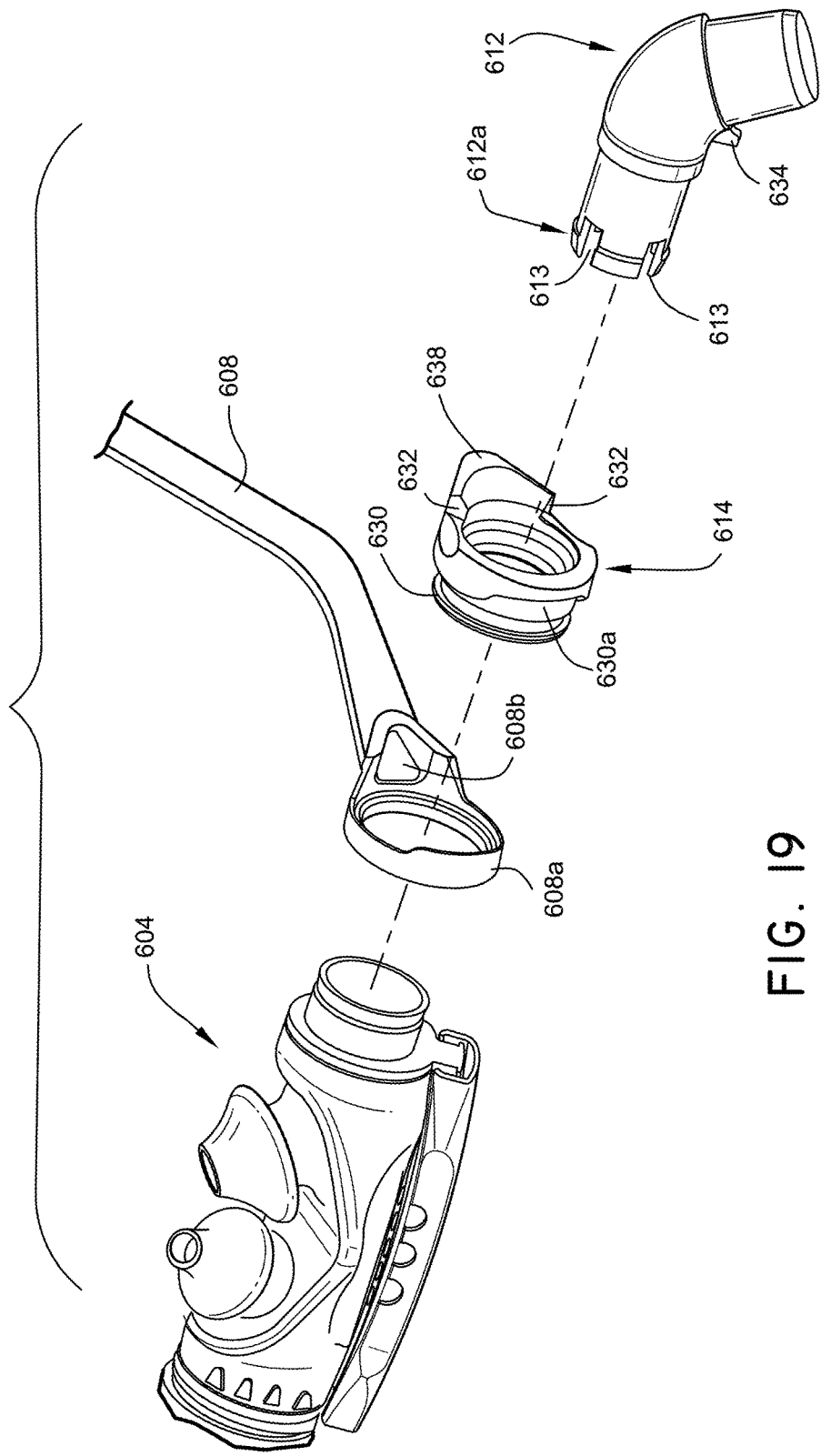
FIGS. 19-31 illustrate yet another embodiment of the present invention.
Figure 20:
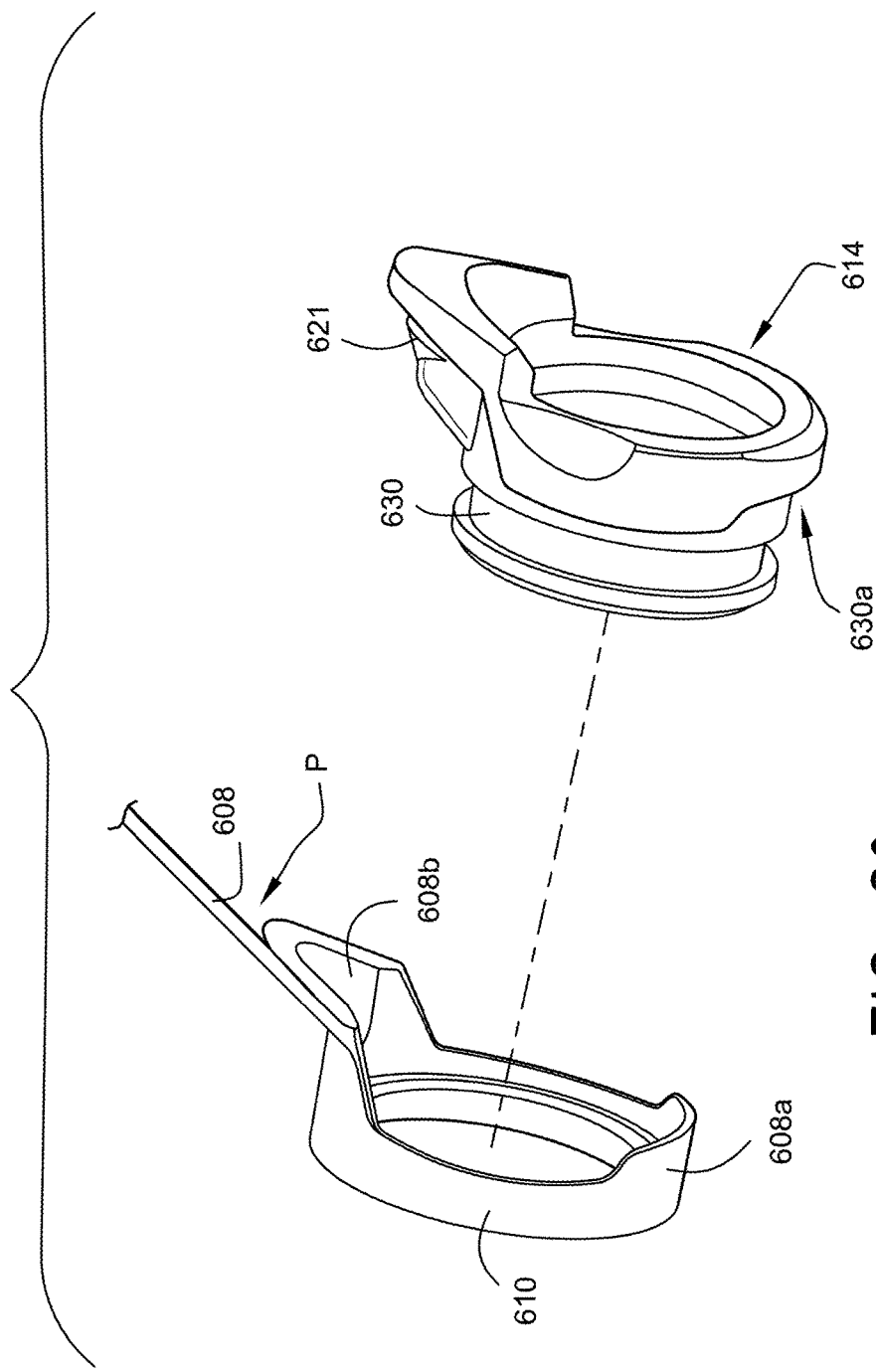

FIG. 19 illustrates a partial exploded view of another embodiment of the present invention. Yoke 608 includes a widened portion 608a intended to engage with a corresponding widened portion 630a adjacent or formed as part of groove 630. In addition, yoke 608 includes a recess 608b intended to receive ear 638 of seal ring 614. In a further embodiment, yoke 608 and seal ring 614 may be formed in one piece. Also, the yoke and headgear could be formed of one piece, instead of using stitching or other fasteners. As can be seen in FIG. 20, the yoke 608 and seal ring 614 can be snap fit relative to one another, e.g., via shoulder 621. By this structure, the yoke and ring are prevented from rotating relative to one another. FIG. 20 also shows the general position of yoke flex point P, which allows a good fit with the patient.

Figure 21:
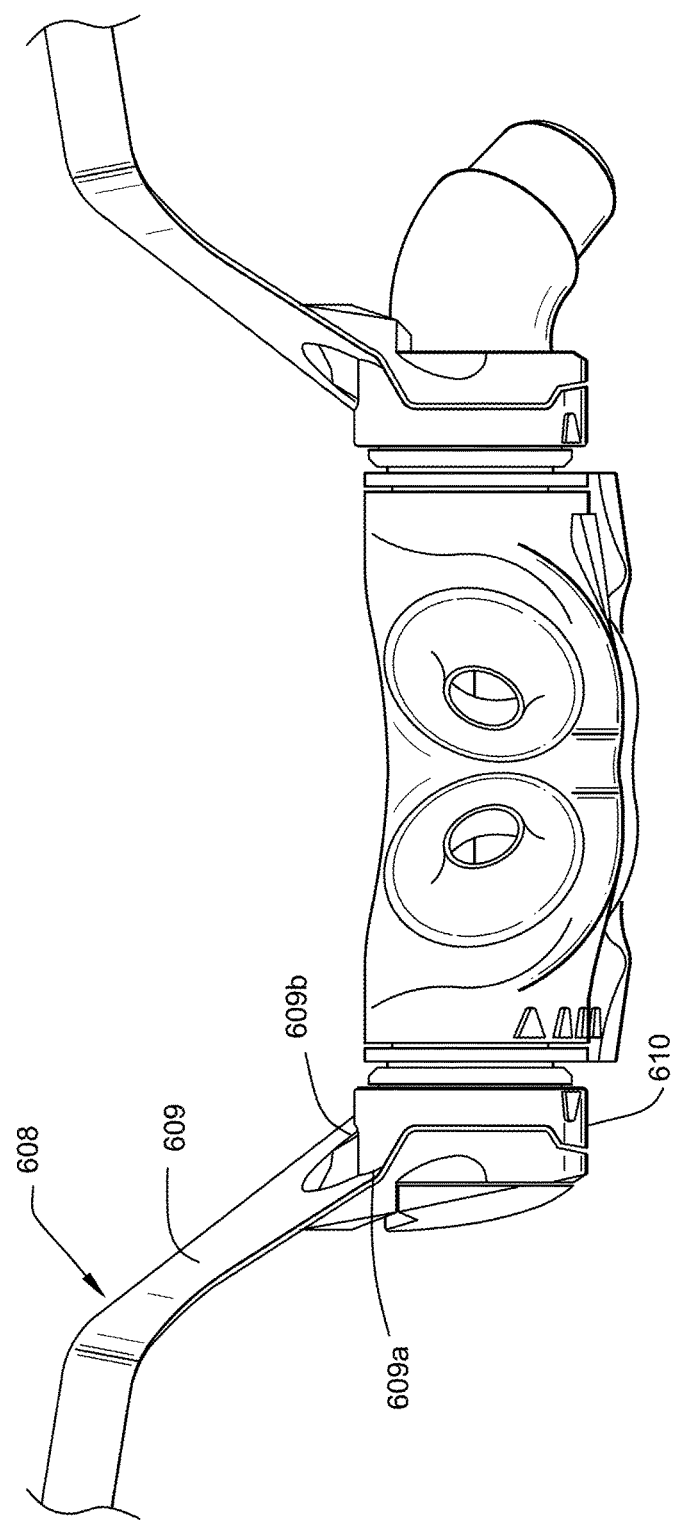
Figure 22:
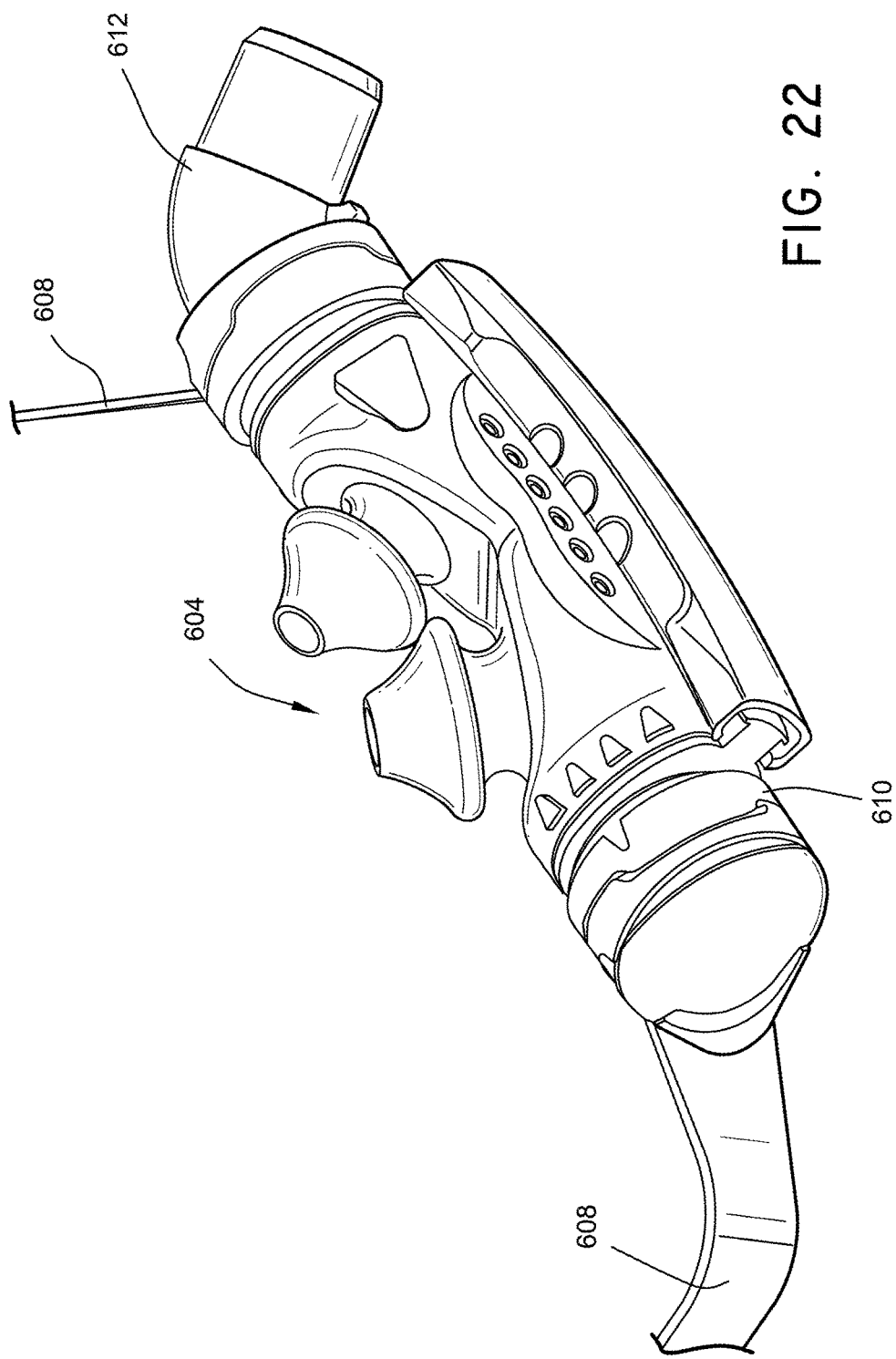
Figure 23:
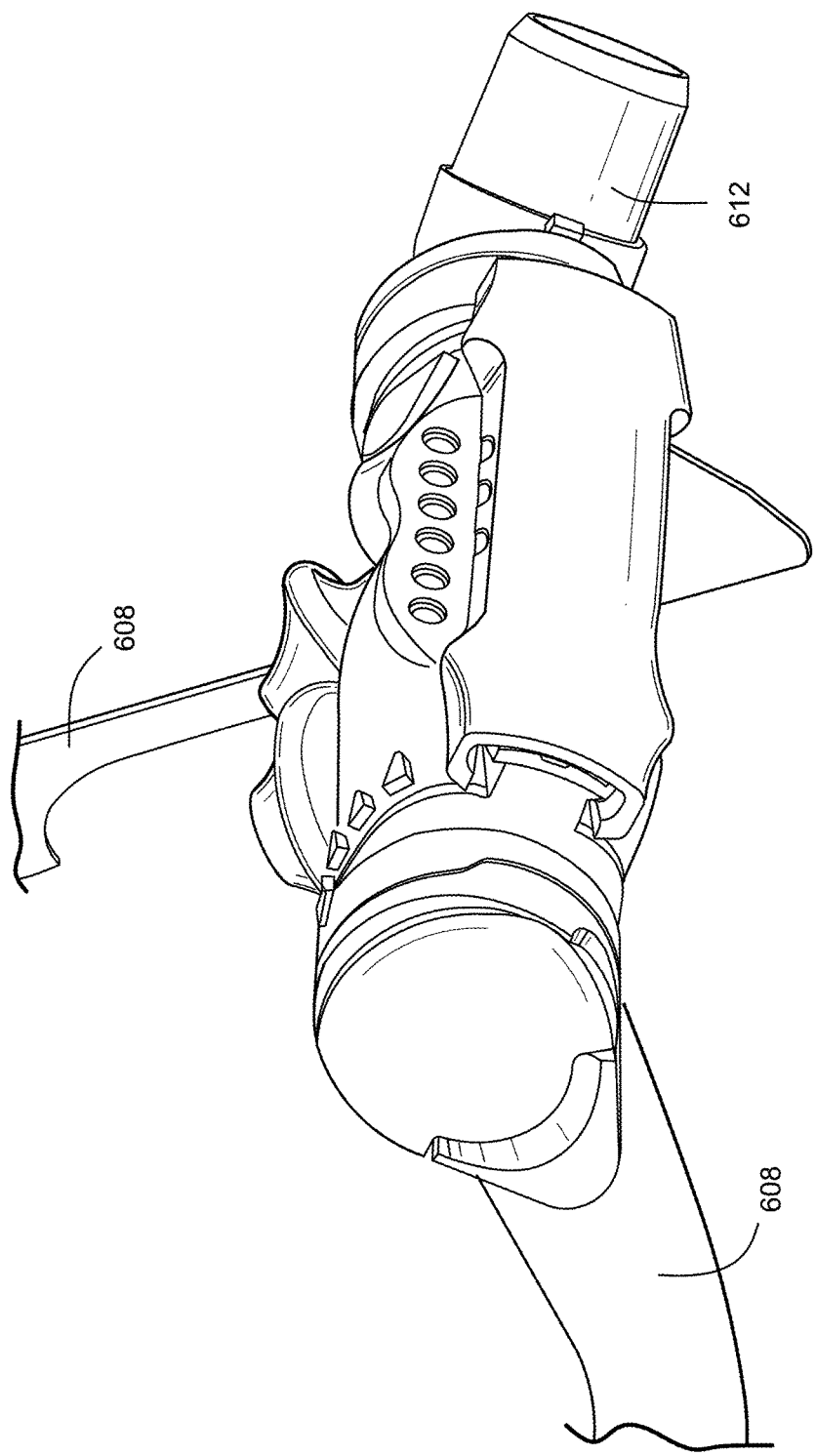
Figure 24:
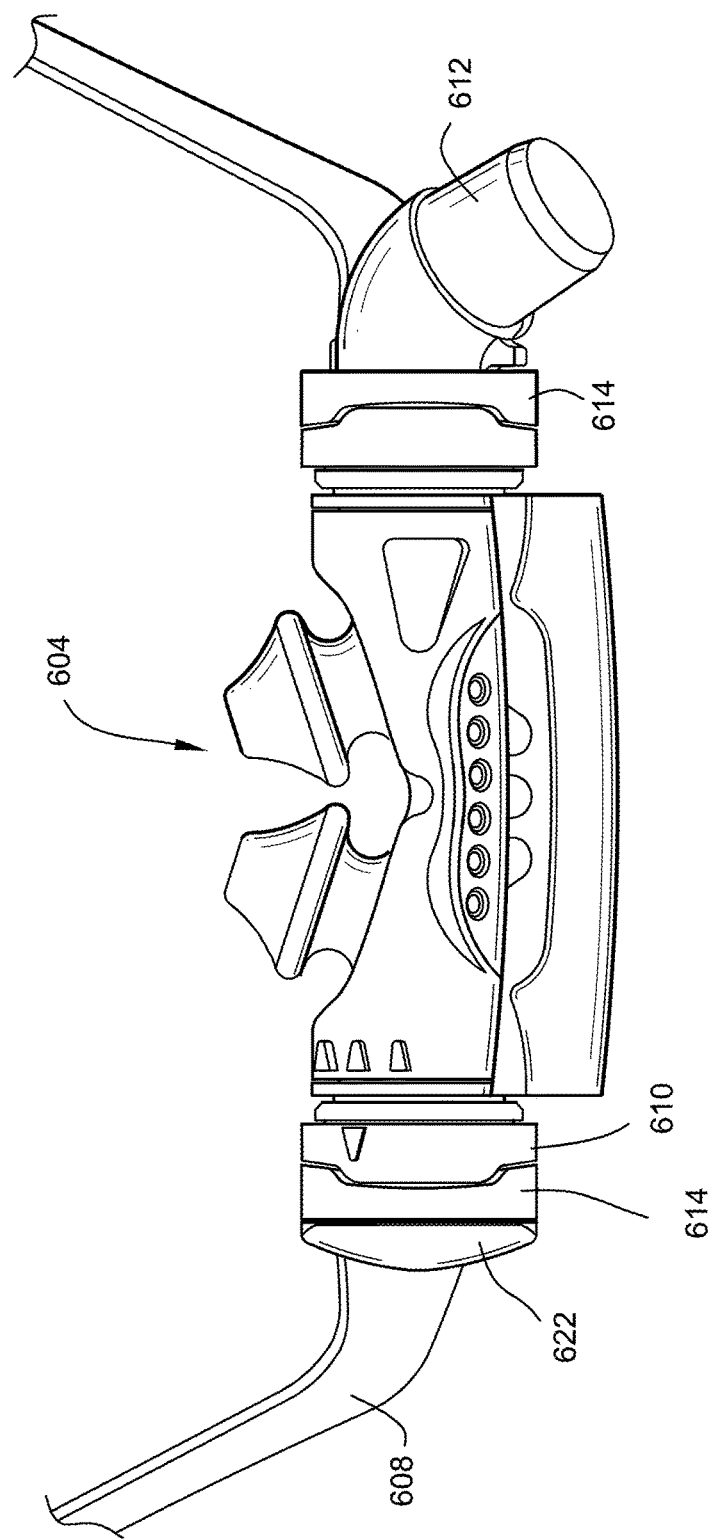
Figure 25:
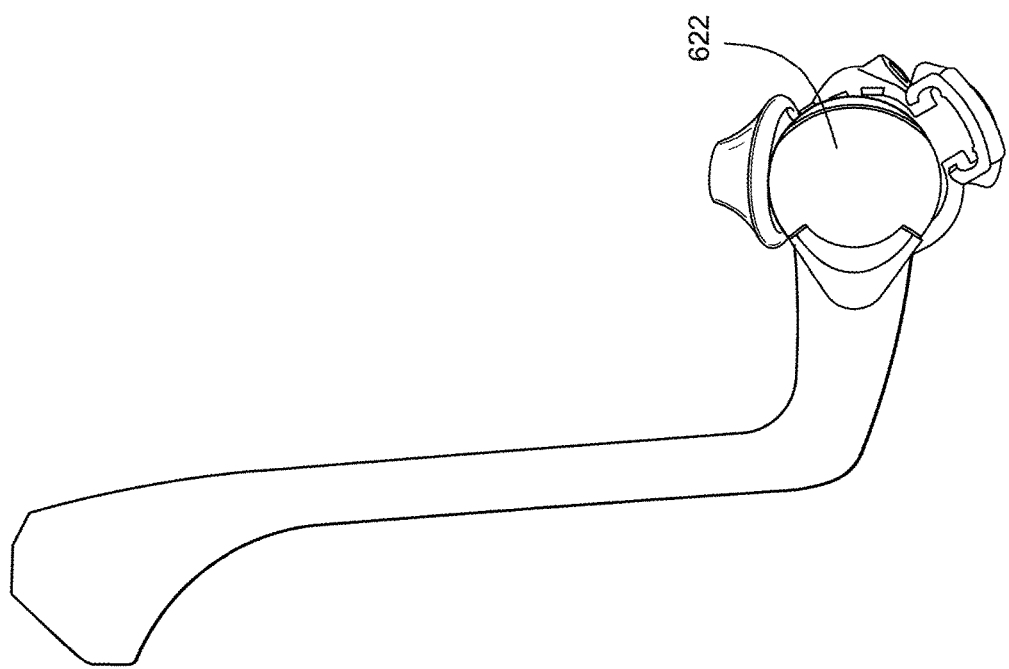
Figure 26:
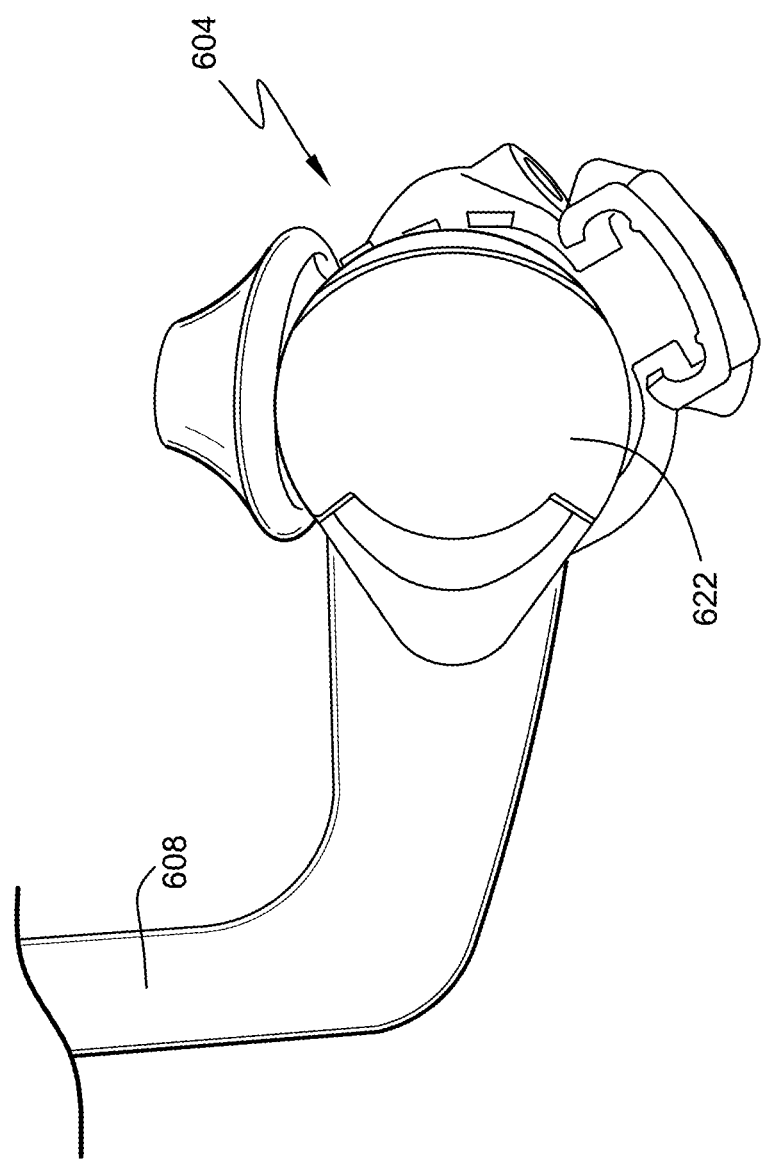
Figure 27:
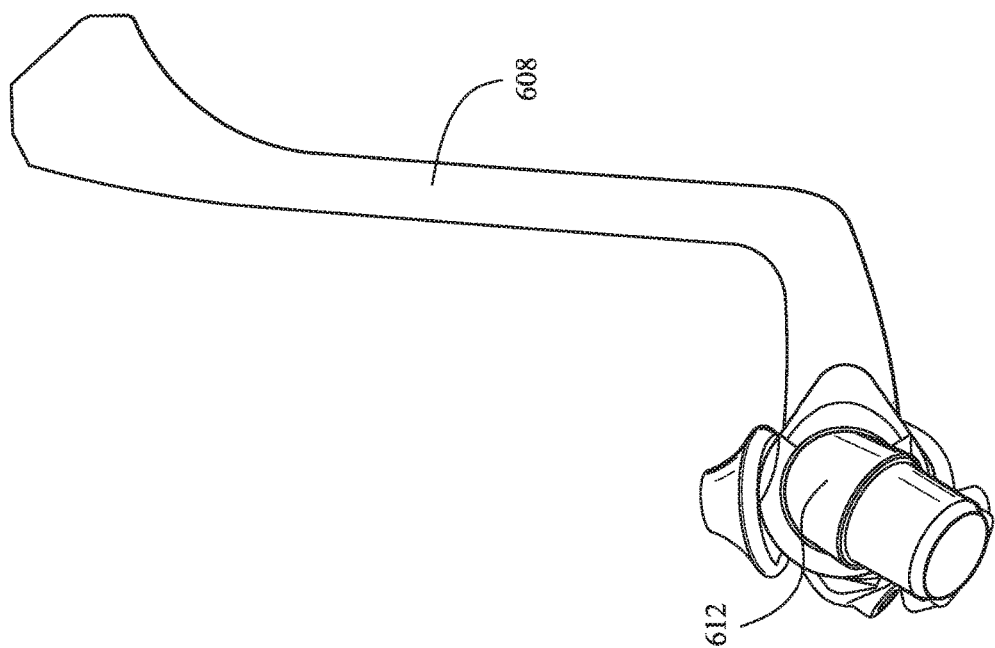
Figure 28:
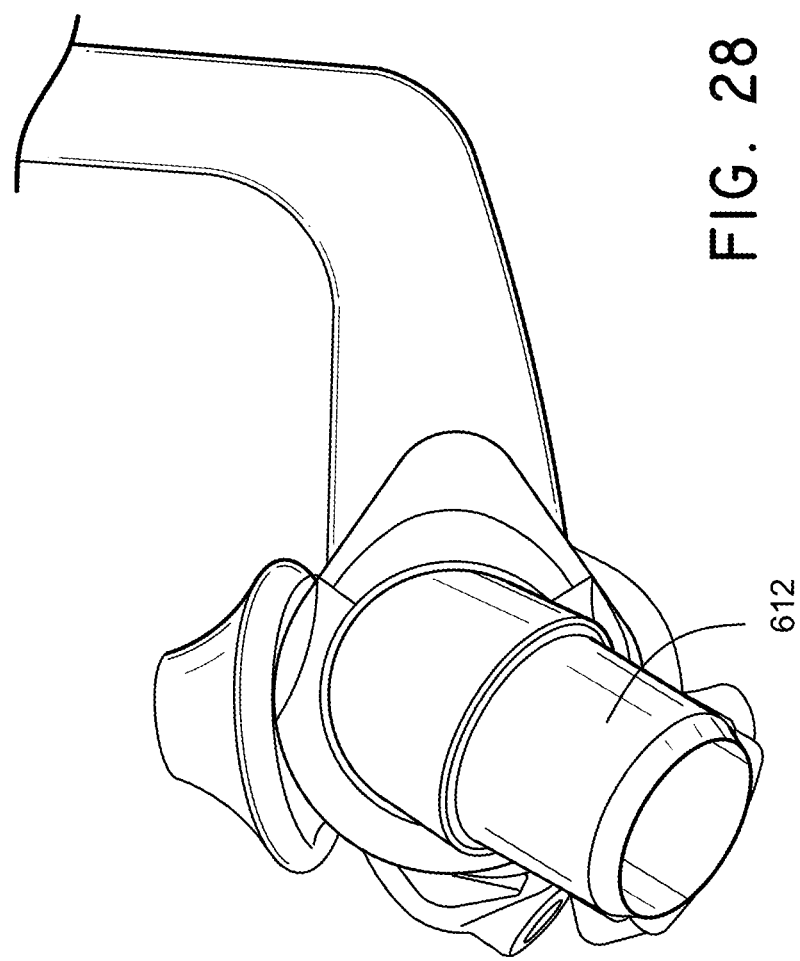
Figure 29:
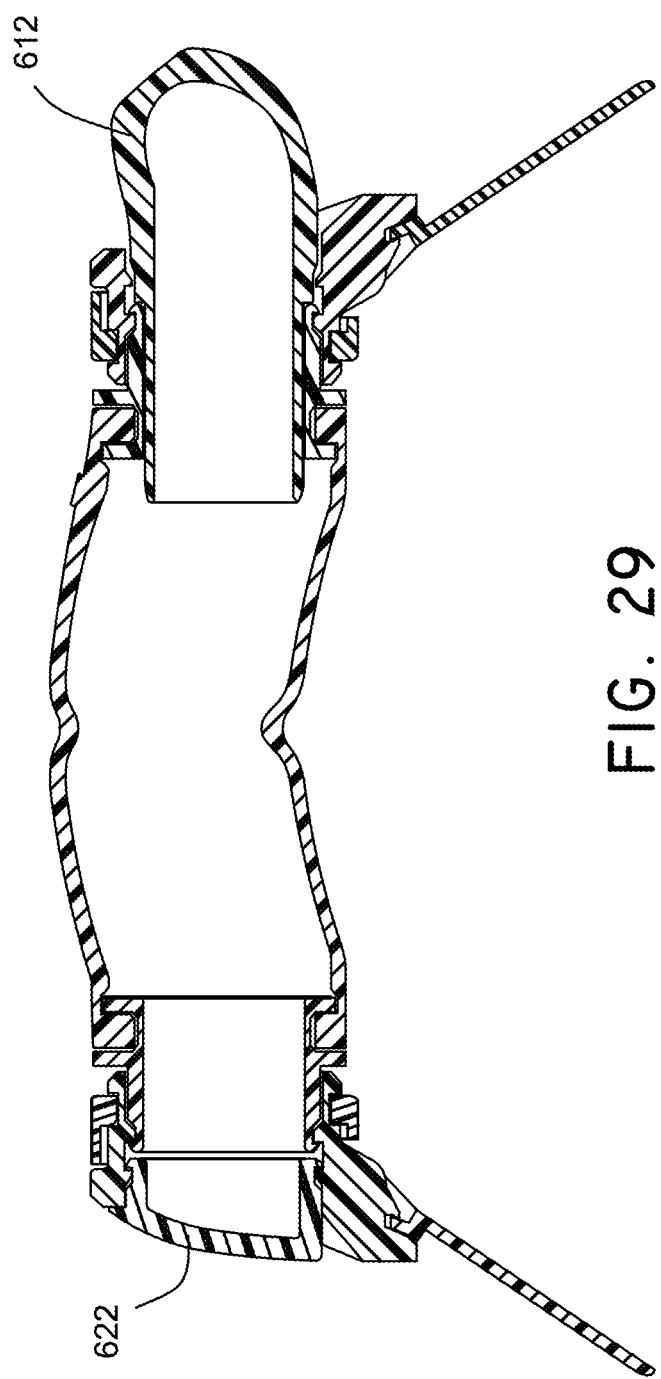
Figure 30:
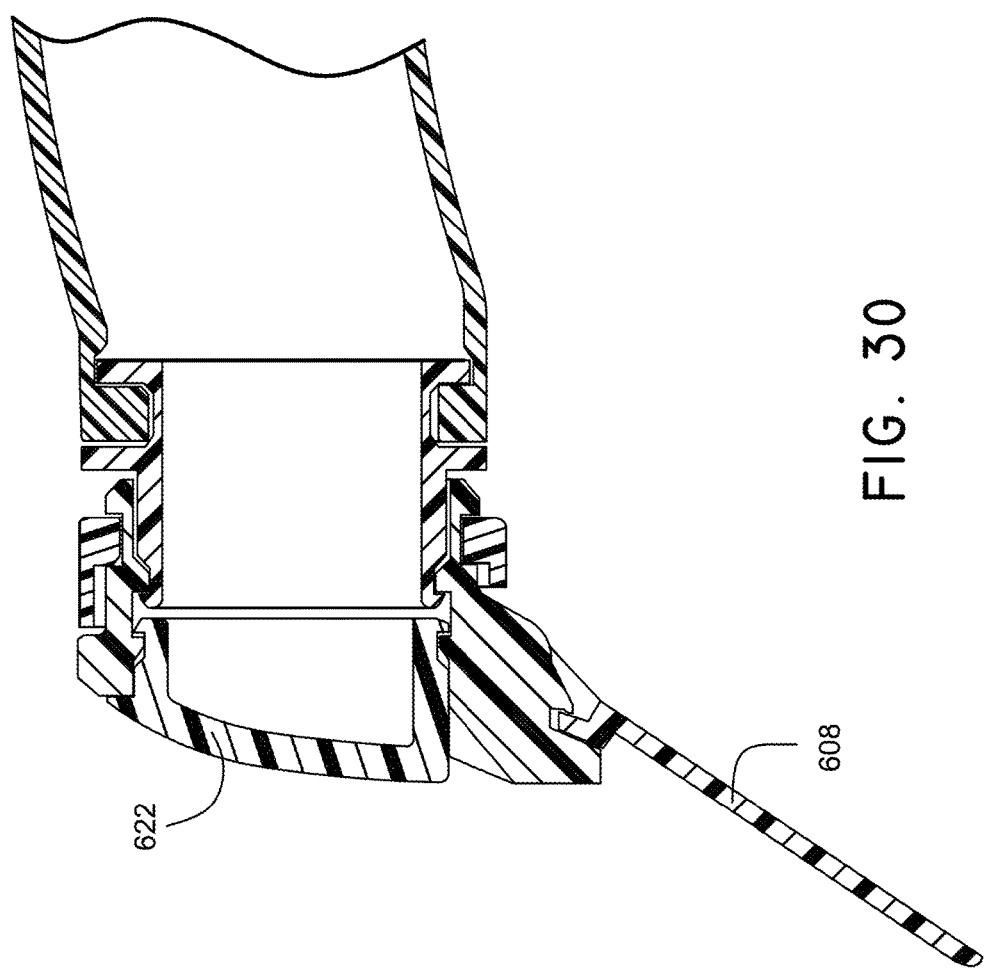
Figure 31:
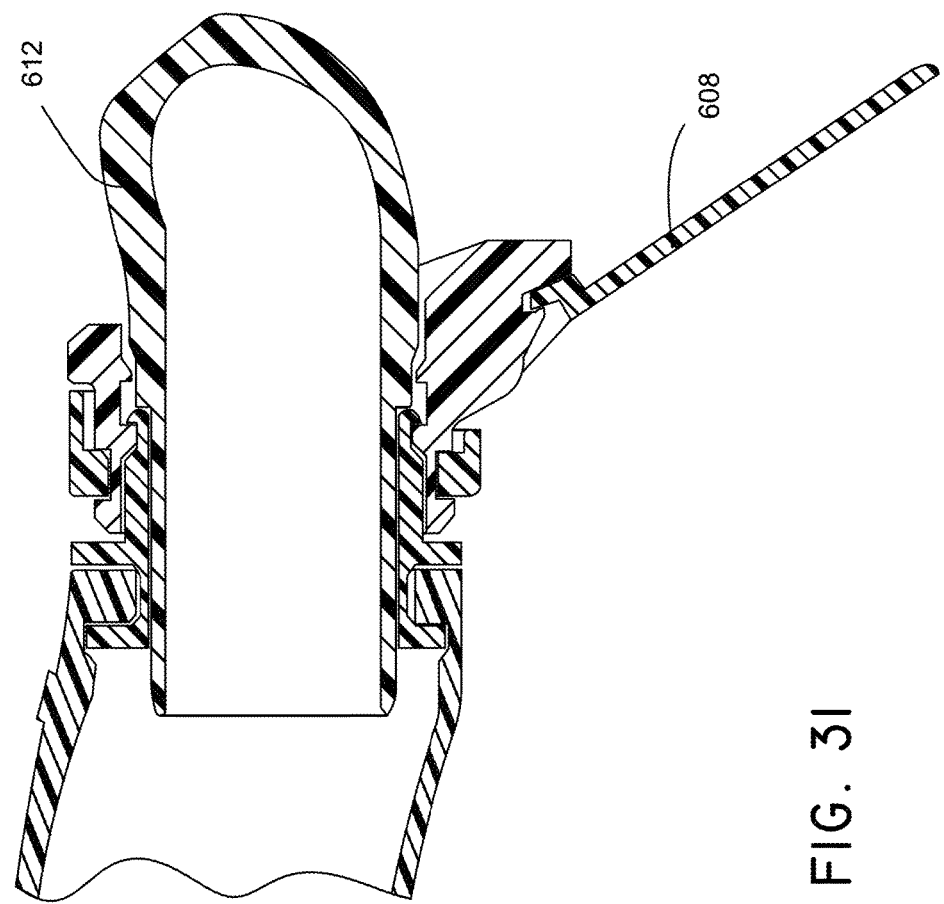
Figure 32:
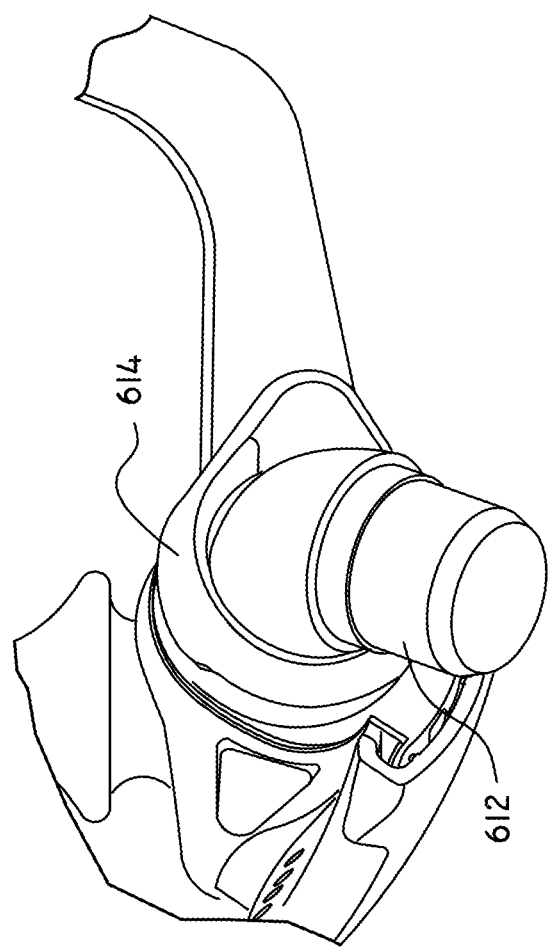
Figure 33:
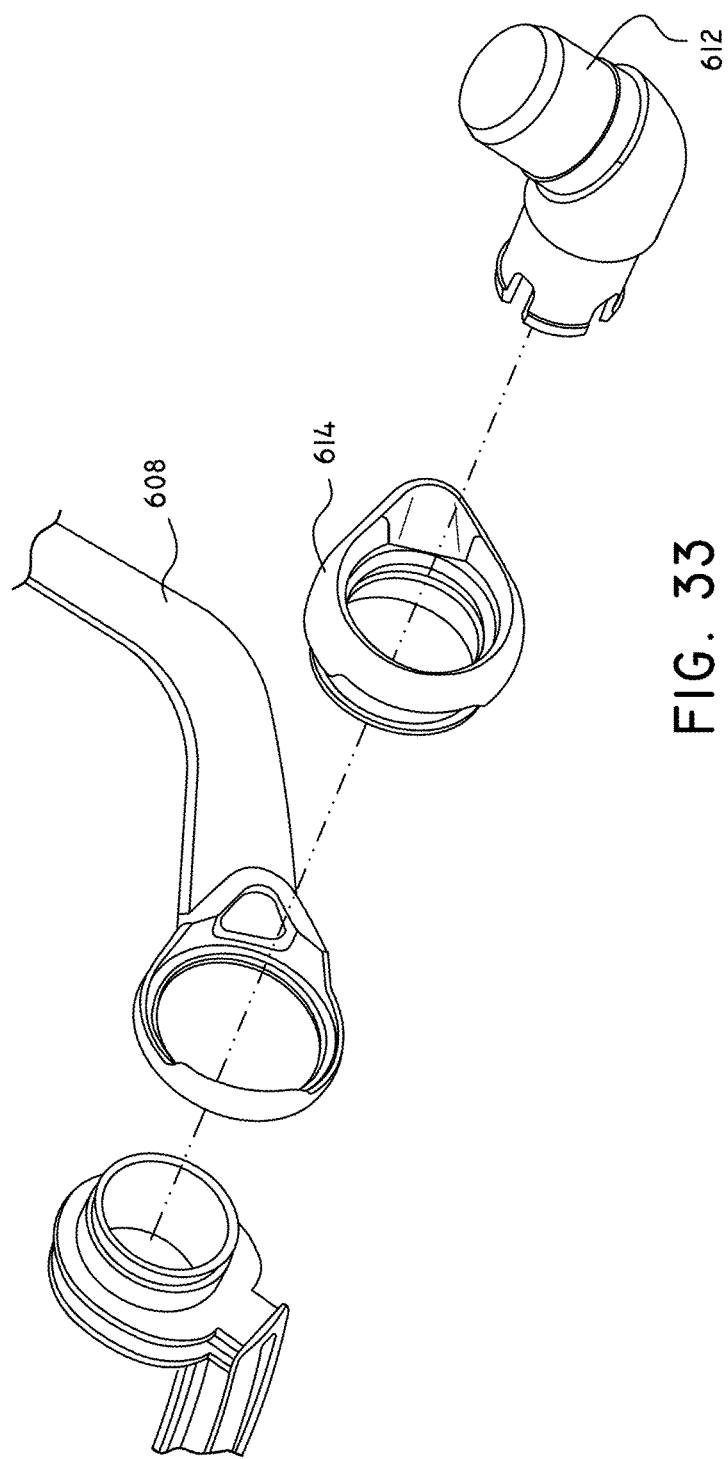

FIGS. 21 to 31 illustrate further views of the embodiment shown in FIGS. 19 and 20. Another aspect of the arrangement is that the ring 610 of the yoke 608 is angularly offset with respect to the main body 609 of the yoke 608. Compare FIG. 21 with FIG. 3, e.g., where the main body 609 in FIG. 21 is twisted. For example, front side 609a in FIG. 21 is positioned laterally outward in comparison to rear side 609b in FIG. 21. This structure helps to bias the bottom portion of the yoke 608 towards the patient's face, so that the yoke more closely follows the contours of the patient's face.

FIGS. 32-35 illustrate a further embodiment of the present invention. This embodiment is similar to that shown and described in FIGS. 19-31. However, there are two main differences. First, the elbow 612 is free to rotate 360° within seal ring 614. As shown in the partial exploded view of FIG. 33, seal ring 614 does not include stops 632 and elbow 612 does not include protrusion 634, as compared to what is shown in FIG. 19.

Figure 34:
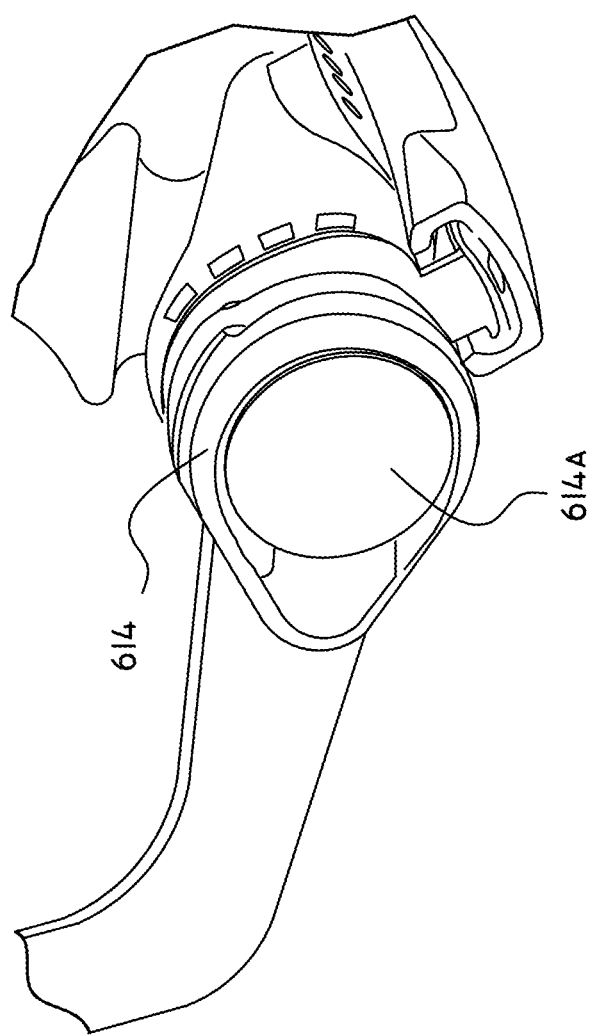

Second, as shown in FIG. 34, seal ring 614 includes a selectively removable and insertable cap 614A. In other words, the plug 622 in FIG. 9 is made in two parts rather than one. The cap 614A may also include or be a vent, instead of or supplemental to the vent provided on the cushion. For example, at least a portion of the outer surface of cap 614A could be structured to allow for the exit of exhaled $CO_2$. The outer surface could include a porous surface, or one with a plurality of holes, as described in U.S. Pat. No. 6,581,594, incorporated herein by reference in its entirety. The outer surface could also include a mesh material, to help vent $CO_2$ in a relatively noise-free manner. FIG. 35 shows a partial exploded view of cap 614A. Because seal rings 614 on both sides of nozzle assembly are identical, the cap 614A and elbow 612 can be removed and swapped, depending on whether the patient opts to have the elbow 612 routed over the left or right side. This can be done while the mask assembly is in use on the patient. Also, the elbow 612 can be removed to allow for patient mobility.

FIGS. 36-41 illustrate a plug 20 according to yet another embodiment of the present invention. Plug 20 is intended to cooperate with a seal, such as seal 614 shown in FIG. 35. Plug 20 includes a first end 22 including an enlarged head portion and a second end 24. Adjacent first end 22 is a enlarged cylindrical portion 26 which forms a shoulder 28 with respect to a central portion of tube 20 between first and second ends 22 and 24. Second end 24 includes a slightly enlarged, ring-shaped portion 30. Plug 20 includes one and preferably a pair of key-shaped apertures 32. Plug 20 may be made of polypropylene, e.g., Borealis™, or polyester. The shape of aperture 32 allows for improved retention and removal forces, when the plug 20 is in place and when it is removed. See FIGS. 36-40. The plug 20 is shown in the assembled position in FIG. 17.

Figure 41:
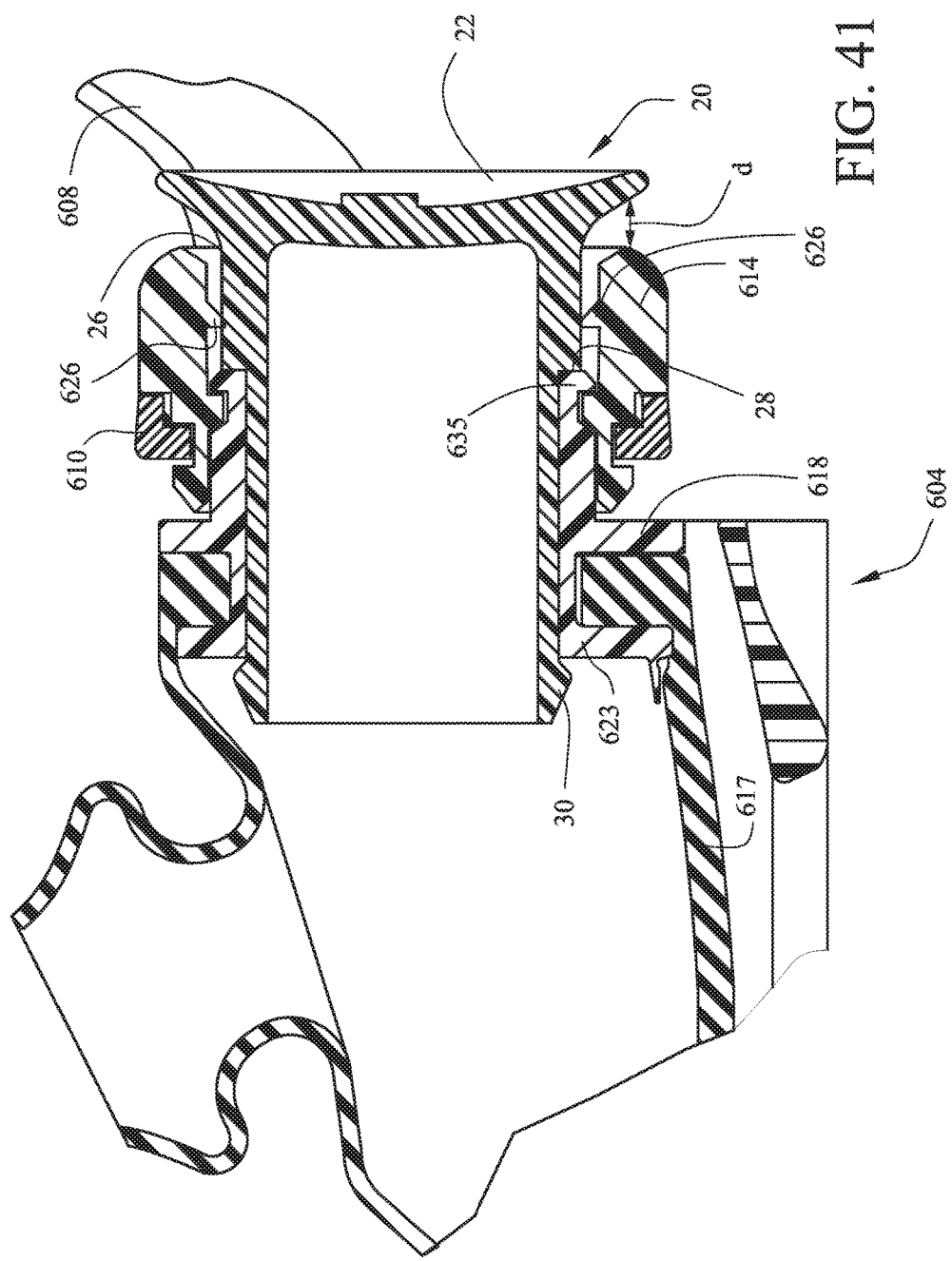

FIG. 41 illustrates a partial cross-sectional view of plug 20 in position with respect to nozzle assembly 604. As shown, enlarged portion 30 is inserted into first connector portion 618. During the insertion process, second end 24 is slightly compressed in the radial sense (via apertures 32) until enlarged portion 30 overcomes the inner edge 623 of first connector portion 618. Upon reaching the inner edge 623, enlarged portion 30 springs outwardly to thereby fix plug in relation to nozzle assembly 604. In that position, seal portions 626 of seal ring 614 form an airtight seal against the outer surface of cylindrical portion 26. In addition, shoulder 28 abuts against end 635 of first connector portion 618. As such, the enlarged head of first end 22 extends a distance d that is spaced slightly away from the end of seal ring 614. For example, distance d is about 1-10 mm or more, but preferably about 3-5 mm. Therefore, the patient or physician can easily grasp enlarged head portion of first end 22 to thereby remove plug 20, for example, in the event that plug 20 and swivel elbow 612 are to be swapped in accordance with the preference of the clinician or patient. The enlarged head may have a concave outer surface, as seen in FIG. 41.

Figure 42:
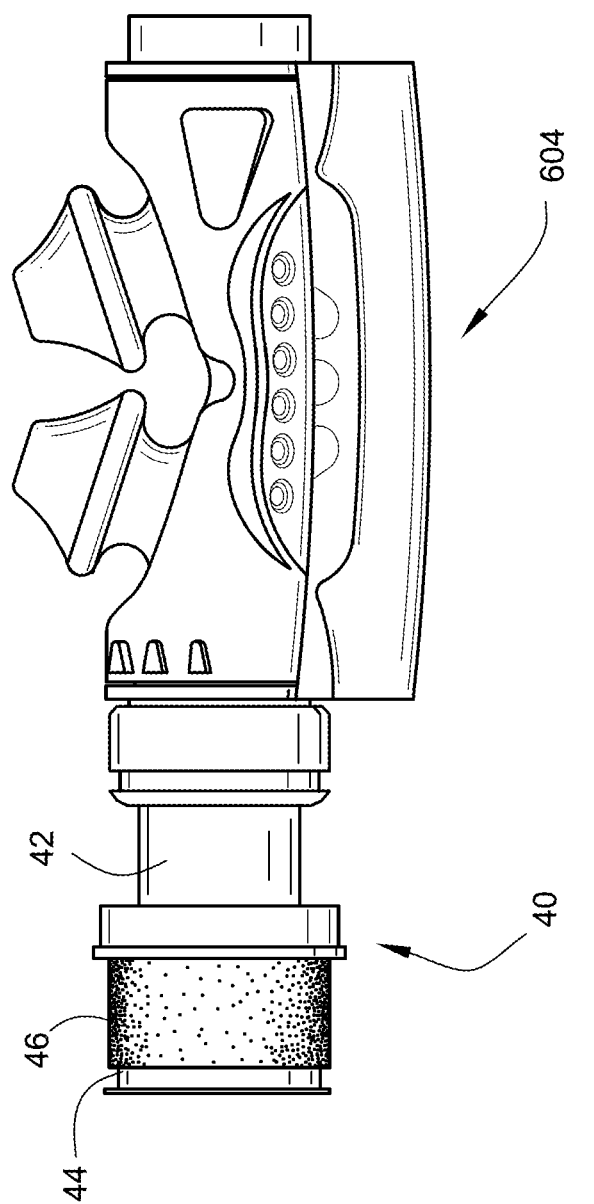
FIG. 42 illustrates a vent in accordance with an embodiment of the present invention.

FIG. 42 illustrates a plug 40 in accordance with yet another embodiment of the present invention. In FIG. 42, plug 40 is intended to be inserted into one side of nozzle assembly 604, as described above in relation, for example, to the embodiment of FIGS. 36-41. Plug 40 includes a first end 42 and a second end 44. First end 42 is intended to be inserted within nozzle assembly 604. Second end 44 is intended to be provided with a vent 46 which allows for the passage of exhaled gas. In this embodiment, vent 46 may be made of a sintered material. Preferably, the sintered material is hydrophobic and allows for the exit of exhaled gas in a relatively noise free manner. In a preferred embodiment, the vent does not overly extend away from the nozzle assembly 604, i.e., it has a low lateral profile. Accordingly, the vent 46 can be sized so as to fit within seal ring 614 and/or first connector portion of frame 616.

Figure 43:
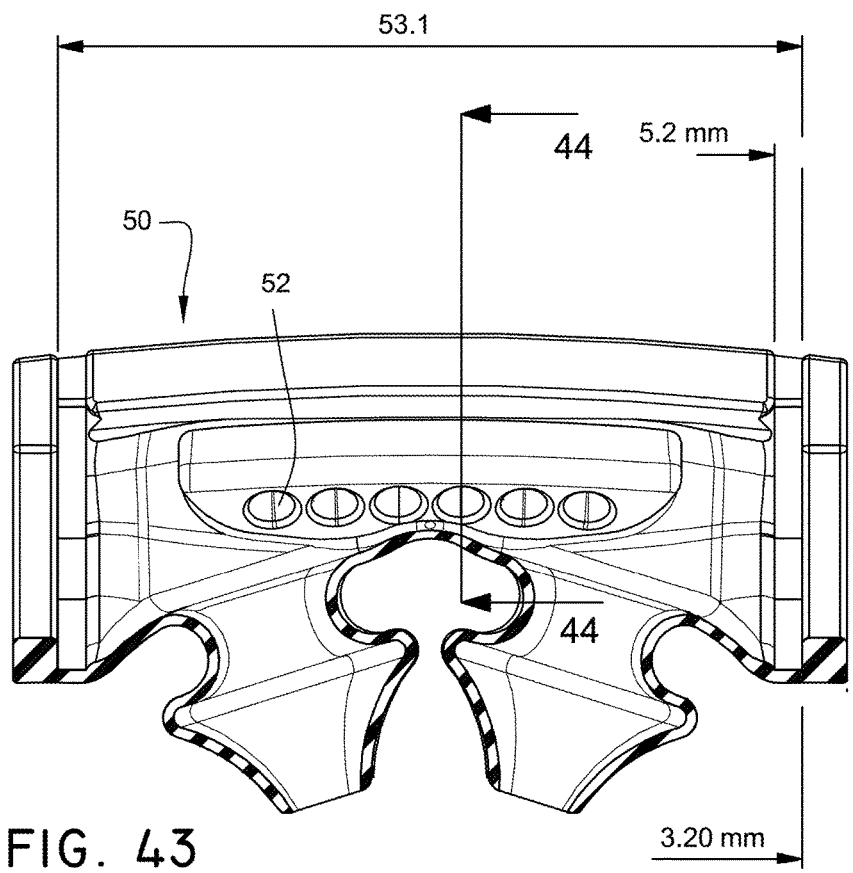
Figure 44:
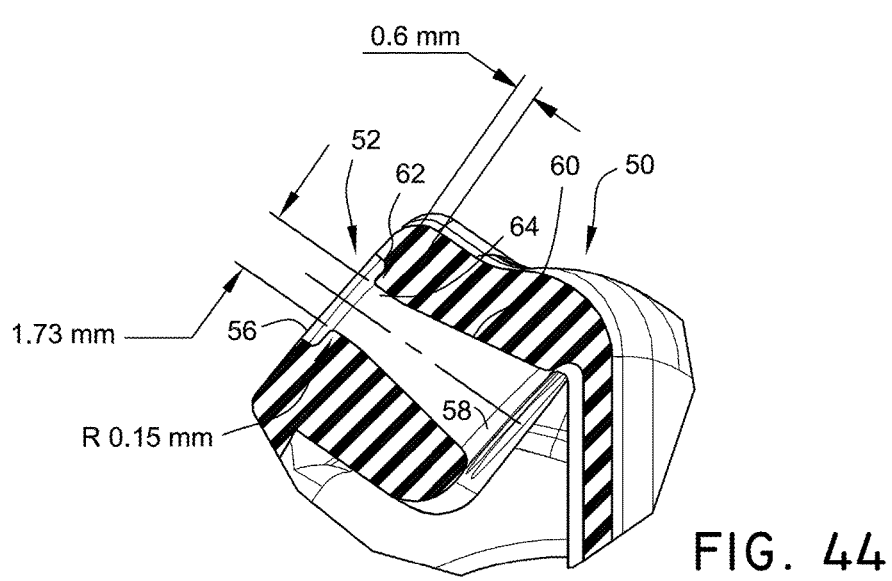

FIGS. 43 and 44 illustrate a cushion 50 according to still another embodiment according to the present invention. Cushion 50 includes one and preferably a plurality of vents 52 to allow passage of exhaled gas from the inside of a plenum chamber formed by the cushion 50. In this example, the cushion 50 includes six vents 52. FIG. 44 is a cross-sectional view along section 44-44 of FIG. 43. Each vent 52 includes a first end 56 oriented towards atmosphere and a second end 58 oriented towards the interior of the plenum chamber. A central portion 60 is provided between first and second ends 56, 58. In a preferred form, the central portion 60 includes a substantially conical section, although other cross-sectional areas and shapes are possible. The vent 52 has a length which is about 4-8 mm or more, and preferably about 6 mm. This increased length as compared to Prior Art FIG. 45B creates a more laminar flow. In addition, the conical shape of central portion 60 allows for easier tooling and removing the silicone part from the tool. The conical profile also appears to create less turbulence upon exiting of the exhaled gas.

First end 56 preferably includes a counter bore 62. In this example, the counter bore has a depth in the range of 0.4 to 0.6 mm or more, and is preferably about 0.5 mm. The diameter is between 2.5 and 5 mm and preferably between 3 and 4 mm. The counter bore 62 has an inside radius of curvature of about 0.1 to 0.2 mm or more, and is preferably about 0.15 mm. As such, it may be possible to reduce or eliminate the flash point from the air path thus preventing significant noise creation. With silicone molding, flash may occur at sharp edges. Therefore, the radius helps to prevent flash. However, a radius that is too large may lead to undesirable noise. Counter bore 62 may be provided to facilitate manufacturing, e.g., in the compression molding process.

A portion 64 is provided adjacent counter bore 62. Portion 64 should preferably have a cylindrical cross-sectional shape, i.e., a substantially straight profile, and forms a transition between the conical central portion 60 and counter bore 62. Portion 64 as formed should have a length of about 0.4 to 0.8 mm or more, and preferably is about 0.6 mm. As such, the hole diameter size for flow can be easily controlled. The minimum hole diameter, e.g., may range from about 1-3 mm, but is preferably about 1.65-1.85 mm, and preferably about 1.75 mm. The diameter at the interior of the conical section may be larger, e.g., in the range of about 3-4 mm or more, and preferably about 3.0-3.6 mm, or about 3.3 mm.

FIGS. 45A and 45C-45H illustrate additional schematic alternatives for the size and shape of the vent 52. In these drawings, a partial rectangular sample portion is shown from several views. In order from left to right, the views of the sample portion include: a cross section through each vent with exemplary dimensions; a view from the atmosphere side; a side view showing the relative thicknesses of the main body of the patient interface; a view from the interior of the patient interface; and a cross-sectional view without dimensions. It should be noted that these exemplary vents could also be provided in a vent insert, an air delivery tube, a tube inlet, e.g., a swivel elbow, and/or a mask frame made of more rigid material, such as polycarbonate. As such, these vent profiles are not limited to use with silicone material or on the patient interface per se. Moreover, the number of holes and the various features of each profile can be combined in any number of ways, each of which are within the scope of this disclosure.

Figure 45:
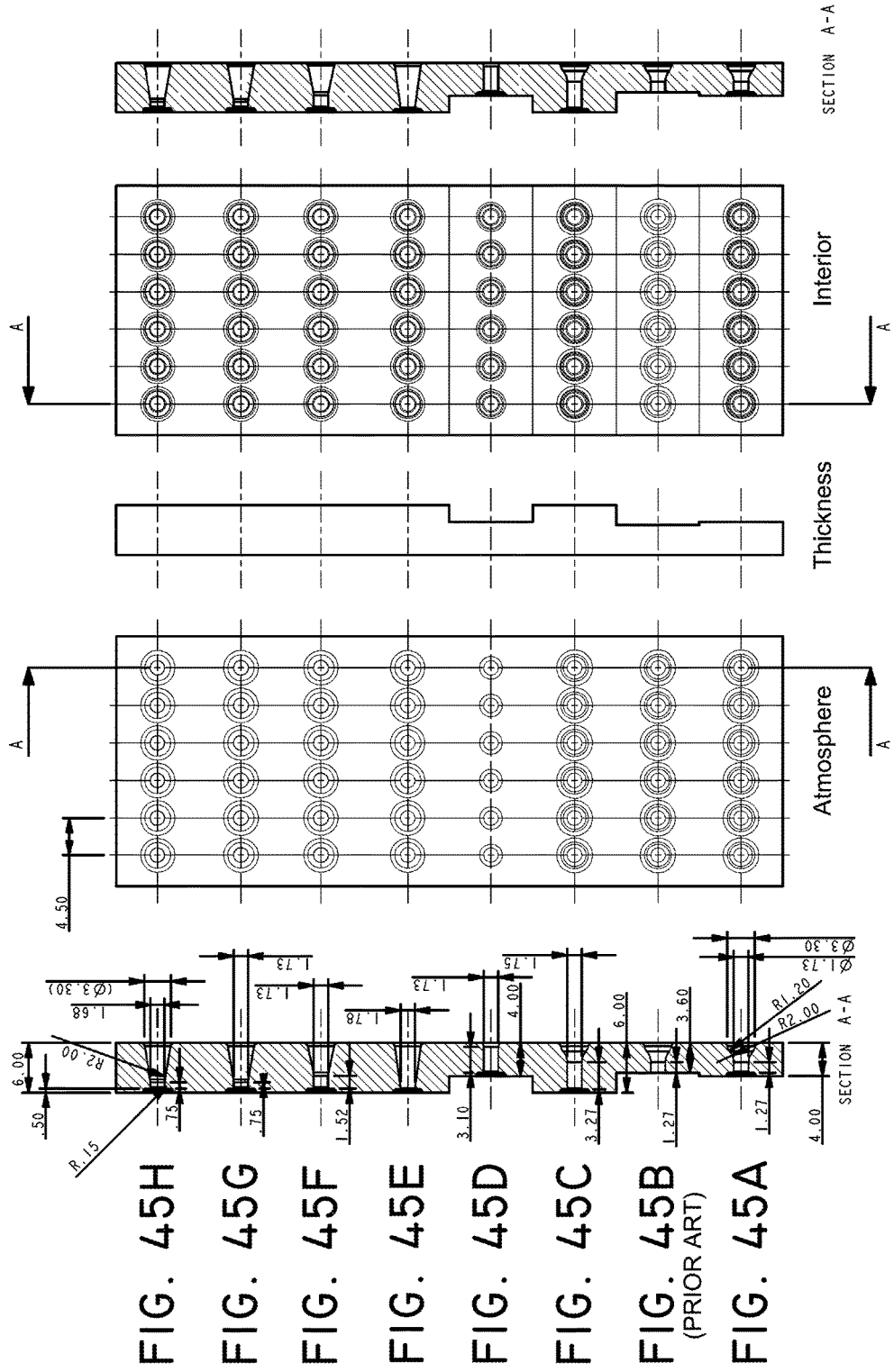

The dimensions shown on FIGS. 45A and 45C-45H are exemplary, and may be changed in accordance with the applicable noise requirements, the number of vents (six in this example), and/or the flow requirements, etc. For example, the minimum diameter ranges from about 1.0 mm or less to 3 mm or more, with preferred examples being shown in FIGS. 45A and 45C-45H. FIG. 45B represents a vent used in the prior art. The embodiment shown in FIG. 45G is similar to that shown in FIG. 44. FIG. 45G illustrates the vent 52 shown in FIG. 44. FIG. 45E is similar to FIG. 45G, but does not include a substantially cylindrical portion, like portion 64 shown in FIG. 44. Portion 64 can vary in length, as can be seen from the comparison of FIGS. 45C and 45F.

Figure 46:
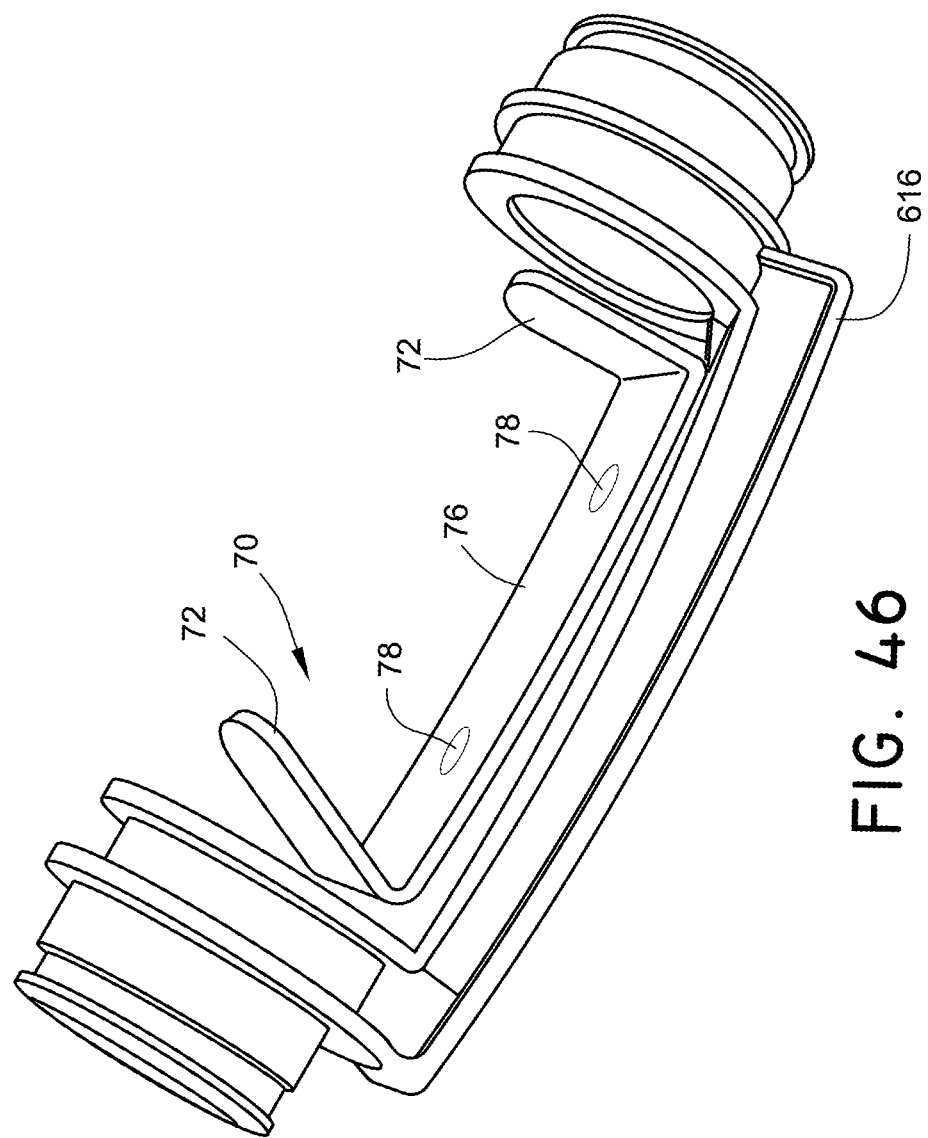
FIGS. 46-48 illustrate baffles in accordance with embodiments of the invention.
Figure 47:
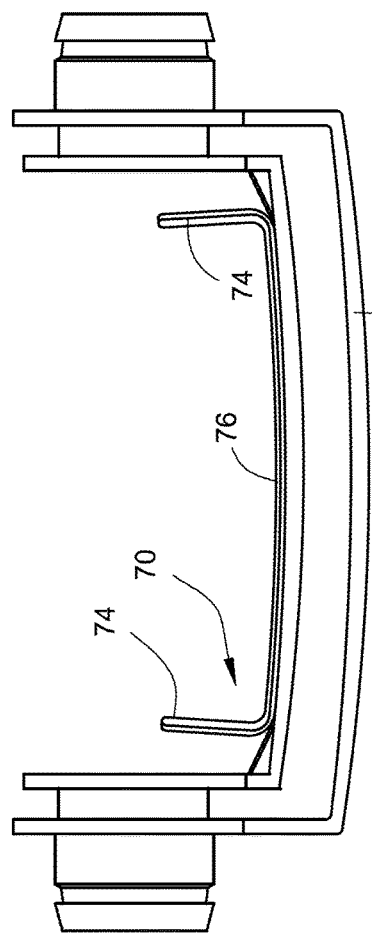
Figure 48:
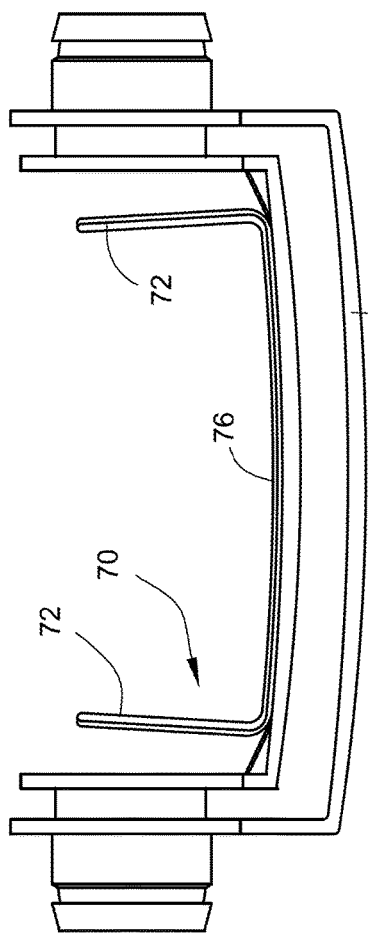

FIGS. 46-48 illustrate baffles 70 in accordance with another embodiment of the present invention. Baffles 70 are shown in conjunction with the frame 616 of nozzle assembly. Frame 616 is similar to the frames described above. The baffle 70 shown in perspective in FIG. 46 is also shown in elevation view in FIG. 48. This baffle includes a pair of arms 72 which are longer than the arms 74 shown in FIG. 47. Baffles 70 help to reduce cyclic noise by creating additional turbulence within the mask and also at least partially separate vent exit from the air inlet which may be beneficial for both noise and minimization of $CO_2$. Baffles 70 include a base plate 76 which supports arms 72, 74. Base plate 76 is connected or otherwise provided to an inside portion of frame 616. For example, as shown in FIG. 46, base plate 76 may include an aperture 78 which is intended to receive a complimentary shaped protrusion provided as part of frame 616.

Figure 49:
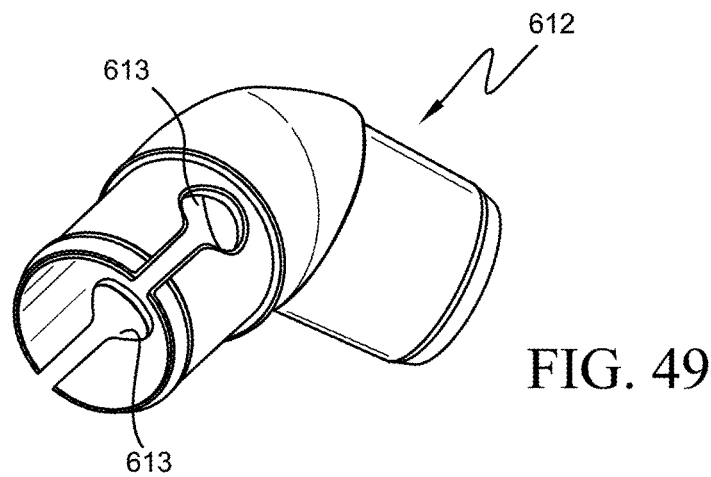
FIGS. 49-51 illustrate yet another swivel elbow according to an embodiment of the invention.
Figure 50:
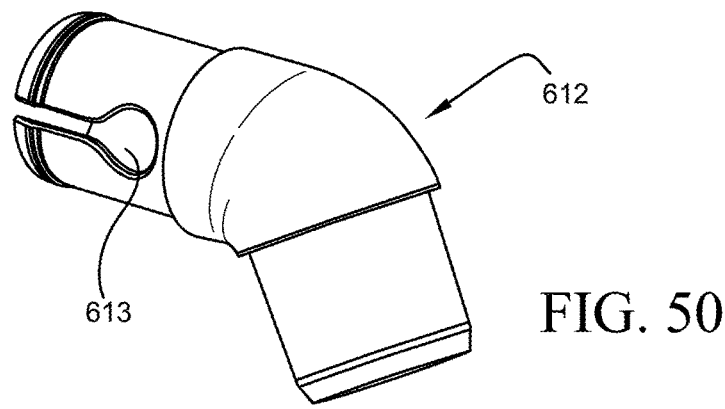
Figure 51:
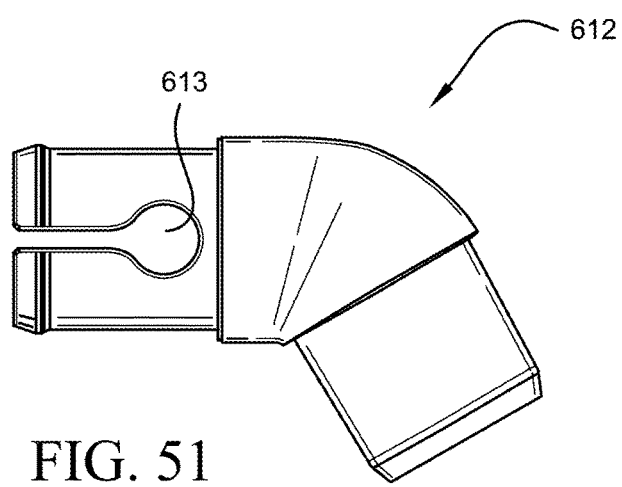

FIGS. 49-51 illustrate an elbow 612 according to yet another embodiment. As compared to elbow 612 shown in FIG. 114, elbow 612 in FIGS. 49-51 includes one and preferably a pair of key-shaped apertures 613. The elbow may be made of polypropylene, e.g., "Borealis," or polyester. The shape of the apertures allows for improved retention and removal forces, when the elbow is in place and when it is removed.

Figure 52:
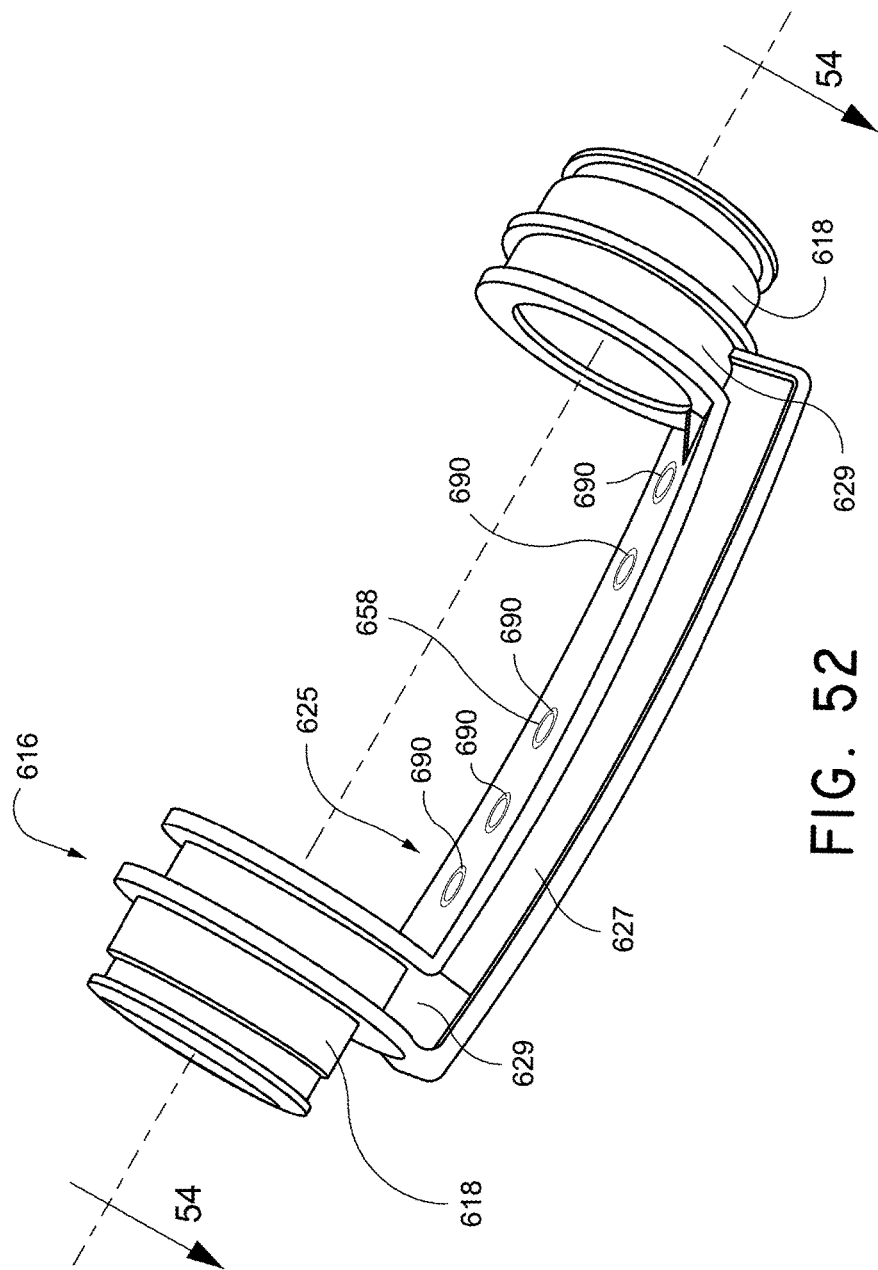

FIGS. 52-54 illustrate a frame 616 according to another embodiment. The frame 616 is substantially similar to the frames described above. In contrast, the frame 616 includes a vent 625 structured to allow for the exit of exhaled gas. The vent 625 may be instead of or supplemental to the vent provided on the cushion and/or plug.

For example, the frame 616 includes a main body 627 and a side frame member 629 provided on each lateral side of the main body 627. Each side frame member 629 includes an integrally formed first connector portion 618. As illustrated, the main body 627 includes a vent 625 in the form of one and preferably a plurality of vent apertures 690 to allow passage of exhaled gas. Each vent aperture 690 may be formed by a separate tube that extends through the main body 627, as best shown in FIG. 54. Preferably, the vent apertures 690 are integrally formed in one piece within the main body 627, e.g., as through holes. However, the vent apertures 690 may be formed in the main body 627 in any other suitable manner.

In the illustrated embodiment, the frame 616 includes five vent apertures 690. However, the frame 616 may have any suitable number vent apertures 690. Also, the vent apertures 690 may be spaced apart from one another in any suitable manner, e.g., equally or unequally spaced apart from one another.

FIG. 54 shows a possible profile of the vent apertures 690. As illustrated, each vent aperture 690 includes a first end 656 oriented towards atmosphere and a second end 658 oriented towards the interior of the plenum chamber formed by the cushion. A central portion 660 is provided between the first and second ends 656, 658. In the illustrated embodiment, the central portion 660 includes a substantially conical shape having a varying diameter that is larger towards the second end 658. This configuration helps to create less turbulence upon exiting of exhaled gas. However, the conical shape may have any suitable size and varying diameter. Moreover, the central portion 660 may have any other suitable shape. For example, the vent apertures 690 may have sizes and shapes such as those vents disclosed in FIGS. 45A and 45C-45H. Further, the configuration, dimension, and number of vent apertures 690 may be modified in any suitable manner in order to provide, e.g., desired noise requirements and/or flow requirements.

Similar to the frames described above, the frame 616 is constructed of a substantially rigid material, e.g., plastic or polycarbonate. The rigid construction enables the frame 616 to be produced with a consistent vent shape and dimension (without rough edges, flash, or damage to the vent apertures), which results in providing a frame 616 with consistently low vent noise and a consistent flow rate.

Additionally, the vent apertures 690 are provided along the entire length of the main body 627 of the frame 616. This arrangement increases the length of the vent path, which reduces the turbulence in the vent apertures 690 and creates a more laminar flow from the vent apertures 690. Thus, less noise is generated from the vent apertures 690.

However, the vent 625 in the main body 627 of the frame 616 may have any other suitable structure to allow for the exit of exhaled gas. For example, the main body 627 may include a porous surface, a mesh material, etc.

Figure 55:
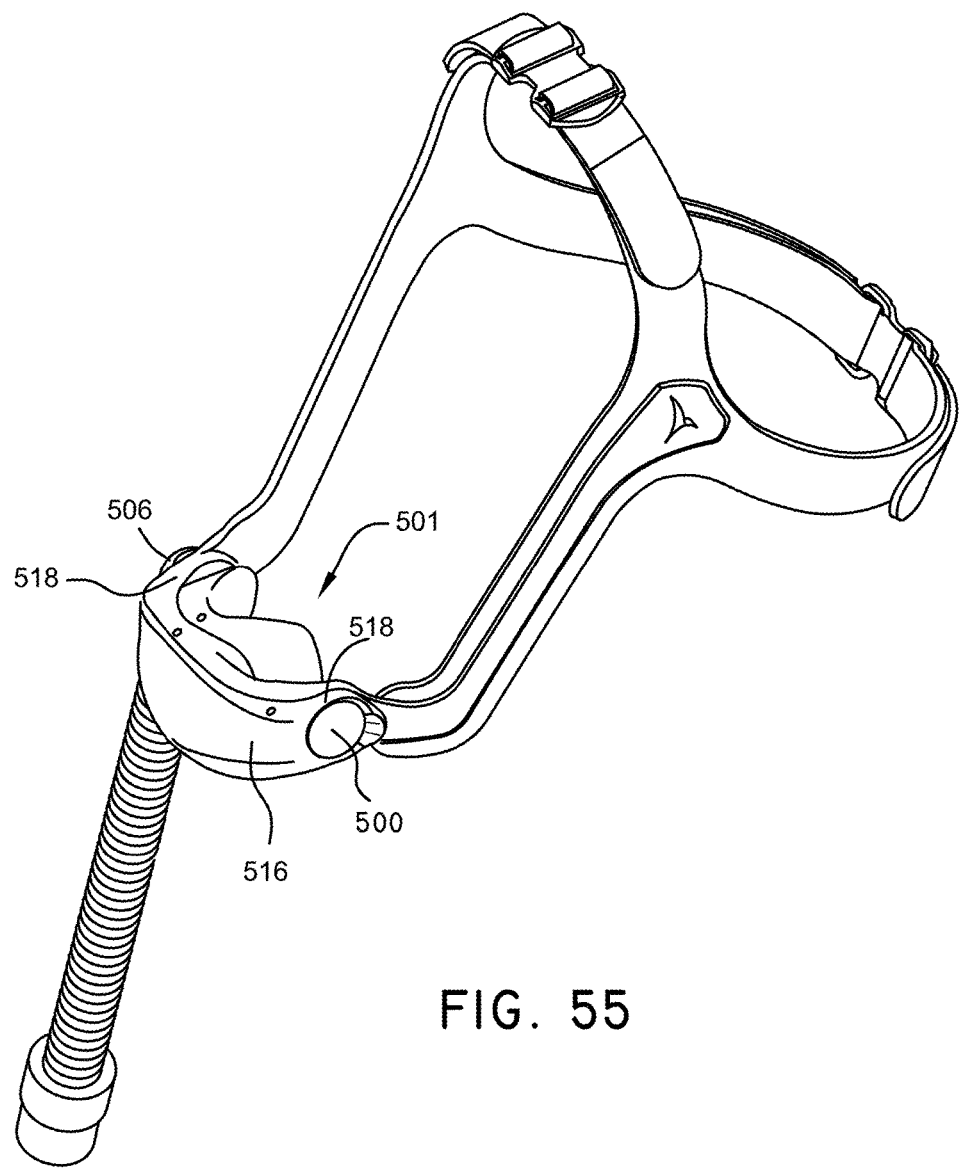
FIGS. 55-58 illustrate further alternative embodiments of the present invention.
Figure 56:
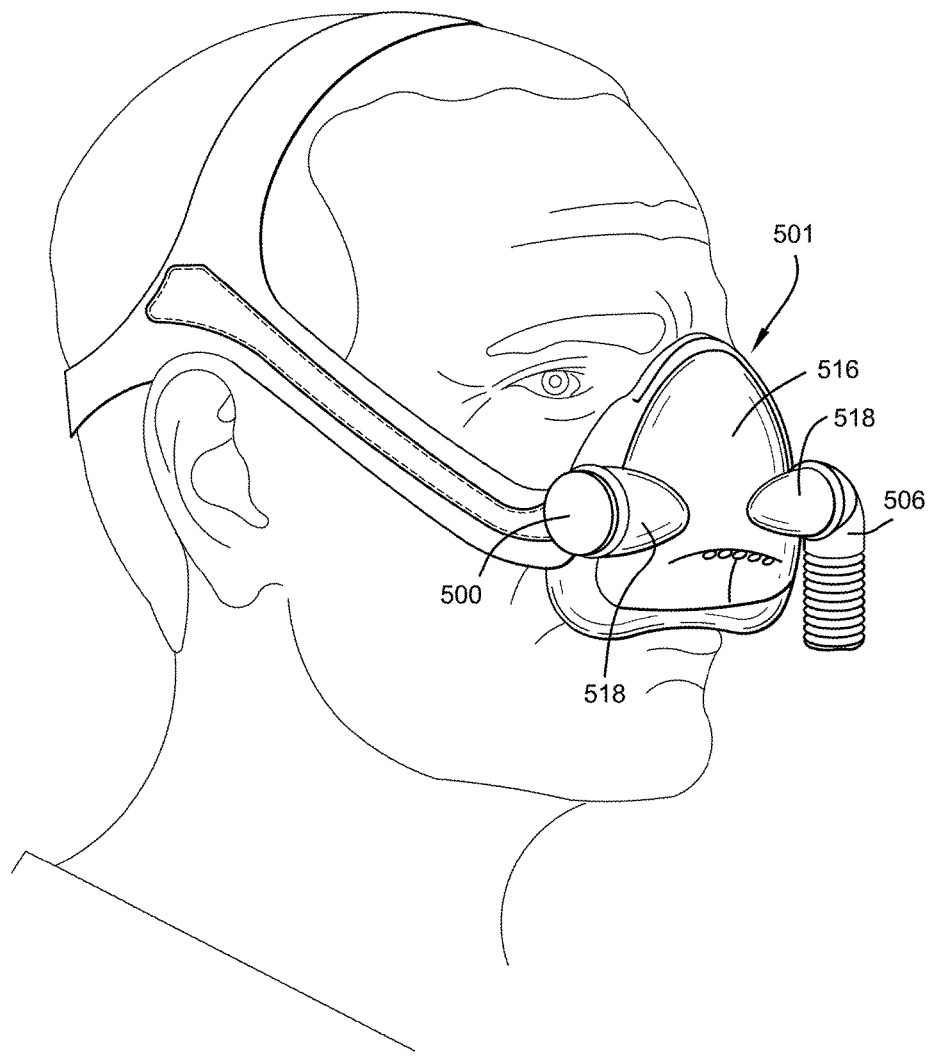
Figure 57:
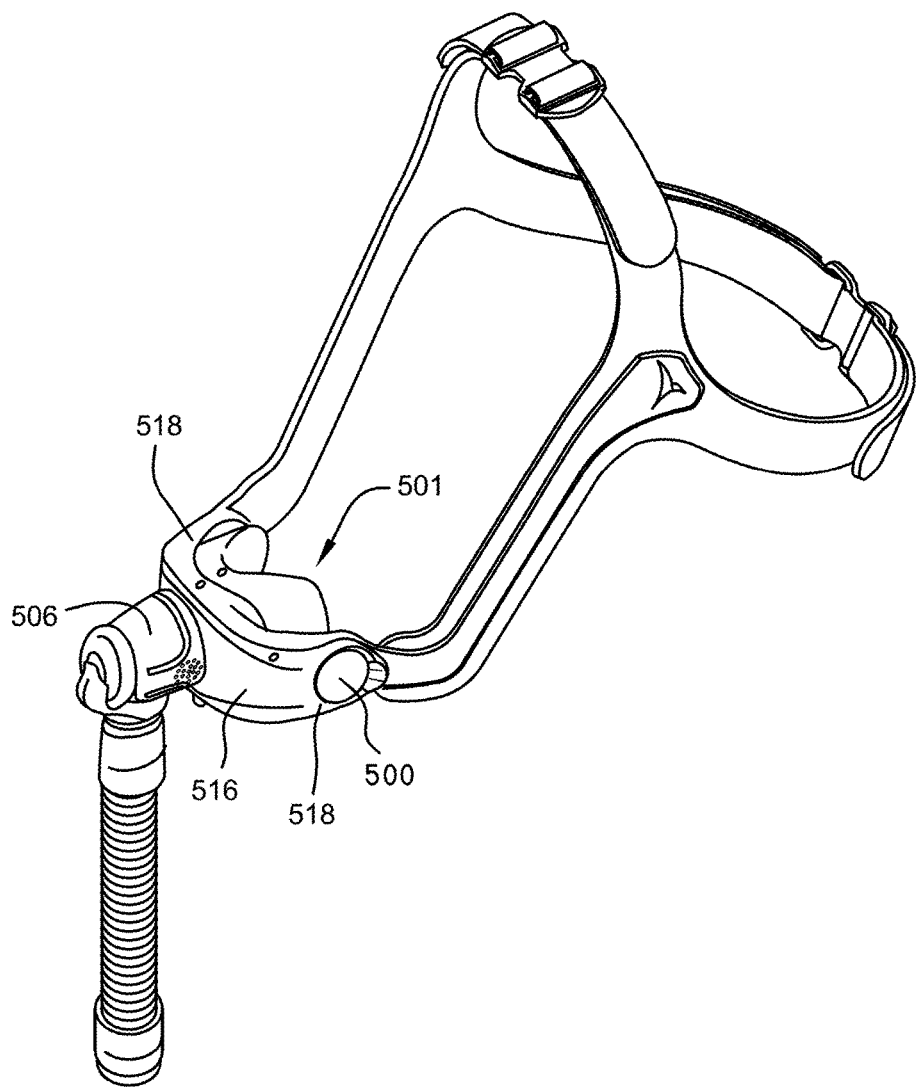

Further, the nozzle assembly and/or its associated cushion could be replaced with a nasal mask and/or nasal cushion 501. See, e.g., FIGS. 55, 56, and 57. FIGS. 55 and 56 show arrangements in which the frame 516 includes opposite apertures or first connector portions 518 (e.g., tubular extensions), each of which is provided with a seal ring as described above. A seal ring is adapted to include a separate or integral plug 500 to close one aperture or first connector portion of the frame, while another seal ring is adapted to engage with the other frame aperture/first connector portion, and to receive the swivel elbow 506. Of course, the positions of the elbow 506 and plug 500 may be interchanged, depending on patient preference. In FIG. 55, the nasal mask is similar to ResMed's VISTA mask with the elbow 506 provided to the side of the mask frame 516. Further details and embodiments of the frame in FIG. 55 are disclosed in U.S. patent application Ser. No. 10/391,440, filed Mar. 19, 2003, the entirety of which is hereby incorporated herein by reference. The nasal cushion 501 in FIG. 55 is structured to sealingly engage lower nasal bridge, cheek, and lip regions of the patient in use. In FIG. 56, the nasal mask includes a nasal cushion 501, having a gusset portion, structured to sealingly engage upper nasal bridge, cheek, and lip regions of the patient in use, such as the patient interface commercially sold under the name of Activa® by ResMed Ltd. Further details and embodiments of the cushion in FIG. 56 are disclosed in U.S. patent application Ser. No. 10/655,622, filed Sep. 5, 2003, the entirety of which is hereby incorporated herein by reference. In FIG. 57, the elbow 506 is provided to the front of the mask frame 516, like ResMed's VISTA mask, while both apertures/first connector portions are provided with plugged seal rings. Further details and embodiments of the elbow in FIG. 57 are disclosed in U.S. patent application Ser. No. 10/390,826, filed Mar. 19, 2003, the entirety of which is hereby incorporated herein by reference. Of course, in each embodiment, frame, elbow, and/or seal ring(s) may be provided with appropriate vents to exhaust exhaled gas from the breathing chamber.

Figure 58:
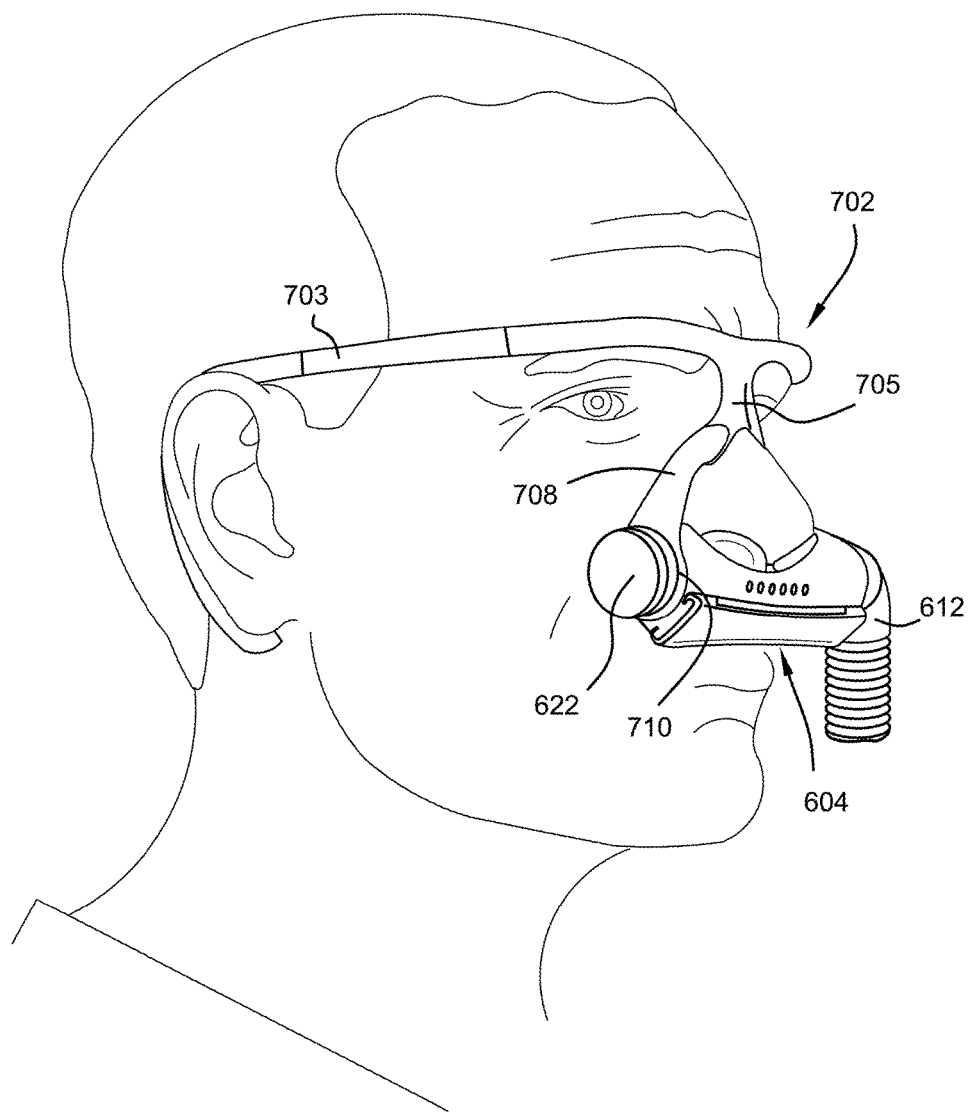

FIG. 58 illustrates another arrangement in which the above-described nozzle assembly 604 is utilized with headgear 702 according to another embodiment of the present invention. As illustrated, the headgear 702 has a spectaclestype construction that provides side portions 703 that wrap around the patient's ears and an intermediate portion 705 that rests on the patient's nose. Yokes 708 extend from the intermediate portion 705 and include yoke rings 710 adapted to engage with respective connector portions provided on the nozzle assembly 604. One end of the cushion assembly 604 is provided with a plug 622 and the other end is provided with a swivel elbow 612. The positions of the swivel elbow 612 and the plug 622 may be interchanged, depending on patient preference. The headgear 702 provide a lightweight and low profile arrangement that may be used as an alternative to headgear 602 to support the nozzle assembly 604 on the patient's head.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability for use with patients and non-patients alike.

What is claimed is:

1. A patient interface for sealed delivery of a flow of breathable gas at a continuously positive pressure with respect to ambient air pressure to an entrance to a patient's airways including at least entrance of a patient's nares, while the patient is sleeping, to ameliorate sleep disordered breathing, the patient interface comprising:
   a patient contacting portion forming a plenum chamber and adapted to sealingly engage with a patient; and
   a vent assembly configured to vent gas from the plenum chamber, the vent assembly including at least one vent having a first end configured to face atmosphere, a second end opposite the first end and configured to face the plenum chamber, and a central portion provided between the first and second ends including a substantially cylindrical cross-ectional shape,
   wherein the first end includes a counter bore, the counter bore of the first end comprising a first diameter,
   wherein the second end includes a counter bore, the counter bore of the second end comprising a second diameter,
   wherein the first diameter is substantially similar to the second diameter, and
   wherein the first and second diameters are relatively larger than a diameter of the central portion.

2. The patient interface according to claim 1, wherein the counter bore of the first end and the counter bore of the second end each includes a depth similar to a depth of the central portion.

3. The patient interface according to claim 1, wherein the second end is structured to reduce or eliminate noise creating flash from an air path.

4. The patient interface according to claim 1, wherein the counter bore of the first end includes a depth similar to a depth of the counter bore of the second end.

5. The patient interface according to claim 1, wherein the patient contacting portion is a nozzle assembly.

6. The patient interface according to claim 1, wherein the patient contacting portion is a nasal cushion.

7. The patient interface according to claim 1, wherein the vent assembly includes at least one vent provided on the patient contacting portion.

8. The patient interface according to claim 1, wherein the vent assembly includes at least one vent provided on a frame that at least in part supports the patient contacting portion.

9. The patient interface according to claim 1, wherein the vent assembly includes a plurality of vents equally spaced apart from one another.

10. The patient interface according to claim 1, wherein the vent assembly includes a plurality of vents unequally spaced apart from one another.

* * * * *

UNITED STATES PATENT AND TRADEMARK OFFICE
CERTIFICATE OF CORRECTION

PATENT NO. : 9,895,505 B2
APPLICATION NO. : 14/259406
DATED : February 20, 2018
INVENTOR(S) : Guney It is certified that error appears in the above-identified patent and that said Letters Patent is hereby corrected as shown below:

In the Claims

In Claim 1, Column 14, Line 3, "substantially cylindrical cross-ectional shape" should be corrected to --substantially cylindrical cross-sectional shape--.

Signed and Sealed this
Twenty-ninth Day of May, 2018

Andrei Iancu
*Director of the United States Patent and Trademark Office*